US011725561B2

(12) United States Patent
Ringstad et al.

(10) Patent No.: US 11,725,561 B2
(45) Date of Patent: Aug. 15, 2023

(54) SYSTEMS AND METHODS FOR SAMPLING EXHAUST GAS

(71) Applicant: Cummins Emission Solutions Inc., Columbus, IN (US)

(72) Inventors: John Ringstad, Oregon, WI (US); Peter Christianson, Waunakee, WI (US)

(73) Assignee: Cummins Emission Solutions Inc., Columbus, IN (US)

( * ) Notice: Subject to any disclaimer, the term of this patent is extended or adjusted under 35 U.S.C. 154(b) by 0 days.

(21) Appl. No.: 17/612,272

(22) PCT Filed: May 21, 2019

(86) PCT No.: PCT/US2019/033354
§ 371 (c)(1),
(2) Date: Nov. 18, 2021

(87) PCT Pub. No.: WO2020/236158
PCT Pub. Date: Nov. 26, 2020

(65) Prior Publication Data
US 2022/0205378 A1  Jun. 30, 2022

(51) Int. Cl.
*F01N 3/20* (2006.01)
*F01N 3/021* (2006.01)
(Continued)

(52) U.S. Cl.
CPC ............ *F01N 3/208* (2013.01); *F01N 3/021* (2013.01); *F01N 11/00* (2013.01); *F01N 13/008* (2013.01);
(Continued)

(58) Field of Classification Search
CPC .......... F01N 3/208; F01N 3/021; F01N 11/00; F01N 13/008; F01N 2560/026;
(Continued)

(56) References Cited

U.S. PATENT DOCUMENTS 4,651,693 A   3/1987 Nakajima et al.
6,843,104 B2  1/2005 Busch
(Continued)

FOREIGN PATENT DOCUMENTS

EP   3 242 122 A1   11/2017

OTHER PUBLICATIONS

International Search Report & Written Opinion for PCT/US2019/033354 dated Aug. 9, 2019, 11 pages.

*Primary Examiner* — Brandon D Lee
(74) *Attorney, Agent, or Firm* — Foley & Lardner LLP

(57) ABSTRACT

A sampling assembly for an exhaust gas aftertreatment system includes a body layer, an outer bowl, a first sampler, and an inner bowl. The body layer defines a cylindrical passage. The outer bowl is coupled to the body layer. The first sampler extends circumferentially along the body layer to the outer bowl. The first sampler includes a first sampler channel and a first sampler aperture. The first sampler channel is configured to provide exhaust gas into the outer bowl. The first sampler aperture is configured to receive the exhaust gas from the cylindrical passage and provide the exhaust gas into the first sampler channel. The inner bowl is disposed at least partially within the outer bowl and configured to receive the exhaust gas from the outer bowl and provide the exhaust gas into the cylindrical passage.

20 Claims, 12 Drawing Sheets

(51) Int. Cl.
*F01N 11/00* (2006.01)
*F01N 13/00* (2010.01)
*G01M 15/10* (2006.01)
*G01N 33/00* (2006.01)

(52) U.S. Cl.
CPC ...... *G01M 15/102* (2013.01); *G01N 33/0037* (2013.01); *F01N 2560/026* (2013.01); *F01N 2560/06* (2013.01); *F01N 2560/14* (2013.01); *F01N 2610/02* (2013.01)

(58) Field of Classification Search
CPC ............. F01N 2560/06; F01N 2560/14; F01N 2610/02; F01N 3/2066; G01M 15/102; G01N 33/0037; Y02T 10/12
See application file for complete search history.

(56) References Cited

U.S. PATENT DOCUMENTS

| | | | |
|---|---|---|---|
| 2005/0160840 A1 | 7/2005 | Allmendinger | |
| 2010/0158758 A1 | 6/2010 | Gustin | |
| 2013/0213013 A1* | 8/2013 | Mitchell | F01N 3/2066 73/23.31 |
| 2014/0150433 A1 | 6/2014 | Van Niekerk et al. | |
| 2014/0199771 A1 | 7/2014 | Piche et al. | |
| 2015/0122002 A1* | 5/2015 | Mackaldener | G01M 15/102 73/114.71 |
| 2017/0191974 A1 | 7/2017 | Tamura | |
| 2017/0191993 A1 | 7/2017 | Tamura | |

* cited by examiner

SYSTEMS AND METHODS FOR SAMPLING EXHAUST GAS

CROSS-REFERENCE TO RELATED APPLICATION

The present application is a National Stage of PCT Application No. PCT/US2019/033354, filed May 21, 2019. The contents of this application are hereby incorporated by reference in their entirety.

TECHNICAL FIELD

The present application relates generally to systems and methods for sampling exhaust gas in an exhaust gas aftertreatment system of an internal combustion engine.

BACKGROUND

For internal combustion engines, such as diesel engines, nitrogen oxide ($NO_x$) compounds may be emitted in exhaust. It may be desirable to reduce NO emissions to comply with environmental regulations, for example. To reduce NO emissions, a reductant may be dosed into the exhaust by a dosing system and within an aftertreatment system. The reductant facilitates conversion of a portion of the exhaust into non-$NO_x$ emissions, such as nitrogen ($N_2$), carbon dioxide ($CO_2$), and water ($H_2O$), thereby reducing NO emissions.

In some applications, it may be desirable to sample a concentration of a constituent, such as $NO_x$, $N_2$, $CO_2$, and/or $H_2O$, in the exhaust gas produced by an internal combustion engine and treated by an aftertreatment system. By sampling the concentration of the constituent, operation of the aftertreatment system can be monitored. This sampling is obtained using a sensor around which the exhaust gas is provided.

The exhaust gas may be provided to the sensor via a sampling tube that extends into and across an exhaust conduit and routes the exhaust gas to the sensor. The sampling tube may disturb the flow of the exhaust gas and thereby increase backpressure and flow induced noise (e.g., turbulence, etc.) in the exhaust conduit. As a result, performance of the internal combustion engine may be negatively impacted.

Additionally, the exhaust gas provided to the sensor may contain liquid in some systems. Over time, this liquid may collect near the sensor. Exposure to liquid can negatively impact the sensor.

SUMMARY

In one embodiment, a sampling assembly for an exhaust gas aftertreatment system includes a body layer, an outer bowl, a first sampler, and an inner bowl. The body layer defines a cylindrical passage. The outer bowl is coupled to the body layer. The first sampler extends circumferentially along the body layer to the outer bowl. The first sampler includes a first sampler channel and a first sampler aperture. The first sampler channel is configured to provide exhaust gas into the outer bowl. The first sampler aperture is configured to receive the exhaust gas from the cylindrical passage and provide the exhaust gas into the first sampler channel. The inner bowl is disposed at least partially within the outer bowl and configured to receive the exhaust gas from the outer bowl and provide the exhaust gas into the cylindrical passage.

In another embodiment, a sampling assembly for use with a $NO_x$ sensor includes a first body layer, an outer bowl, a first sampler, and a $NO_x$ sensor coupling. The first body layer defines a cylindrical passage. The outer bowl is coupled to the first body layer and configured to receive exhaust gas and provide the exhaust gas to the cylindrical passage. The first sampler extends circumferentially along the first body layer to the outer bowl. The first sampler includes a first sampler channel and a first sampler aperture. The first sampler channel is configured to provide the exhaust gas into the outer bowl. The first sampler aperture is configured to receive the exhaust gas from the cylindrical passage and provide the exhaust gas into the first sampler channel. The $NO_x$ sensor coupling is coupled to the outer bowl and includes a $NO_x$ sensor coupling opening that is configured to receive the $NO_x$ sensor.

In yet another embodiment, a sampling assembly includes a body layer, an outer bowl, a first sampler, and a second sampler. The body layer defines a cylindrical passage. The outer bowl is coupled to the body layer and configured to receive exhaust gas and provide the exhaust gas to the cylindrical passage. The first sampler extends circumferentially along the body layer to the outer bowl. The first sampler includes a first sampler channel and a plurality of first sampler apertures. The first sampler channel is configured to provide the exhaust gas into the outer bowl. Each of the plurality of first sampler apertures is configured to receive the exhaust gas from the cylindrical passage and provide the exhaust gas into the first sampler channel. The second sampler extends circumferentially along the body layer to the outer bowl. The second sampler includes a second sampler channel and a plurality of second sampler apertures. The second sampler channel is configured to provide exhaust gas into the outer bowl. Each of the plurality of second sampler apertures is configured to receive the exhaust gas from the cylindrical passage and provide the exhaust gas into the second sampler channel.

BRIEF DESCRIPTION OF THE DRAWINGS

The details of one or more implementations are set forth in the accompanying drawings and the description below. Other features, aspects, and advantages of the disclosure will become apparent from the description, the drawings, and the claims, in which:

Figure 1:
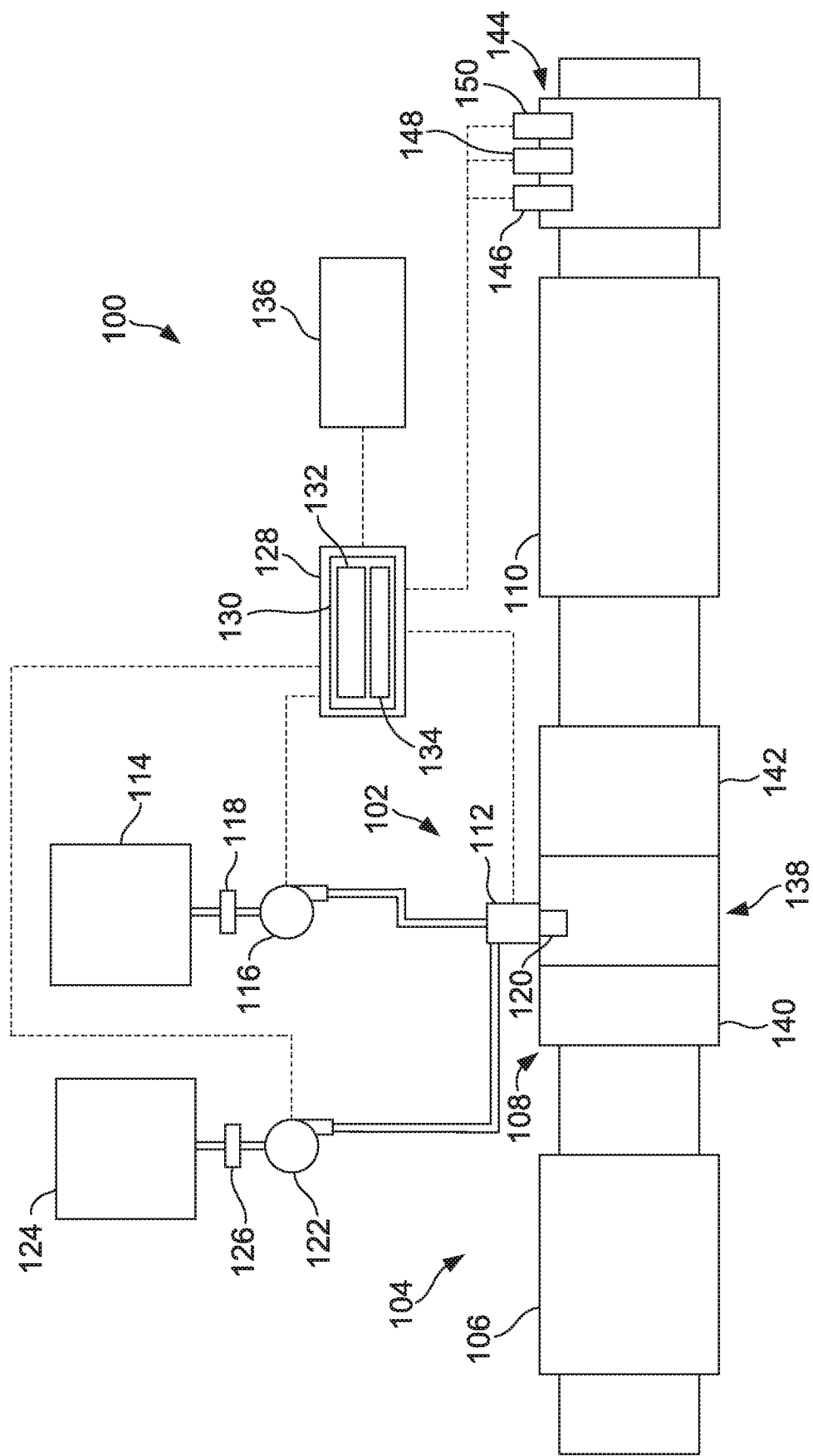
FIG. 1 is a block schematic diagram of an example exhaust gas aftertreatment system.
Figure 2:
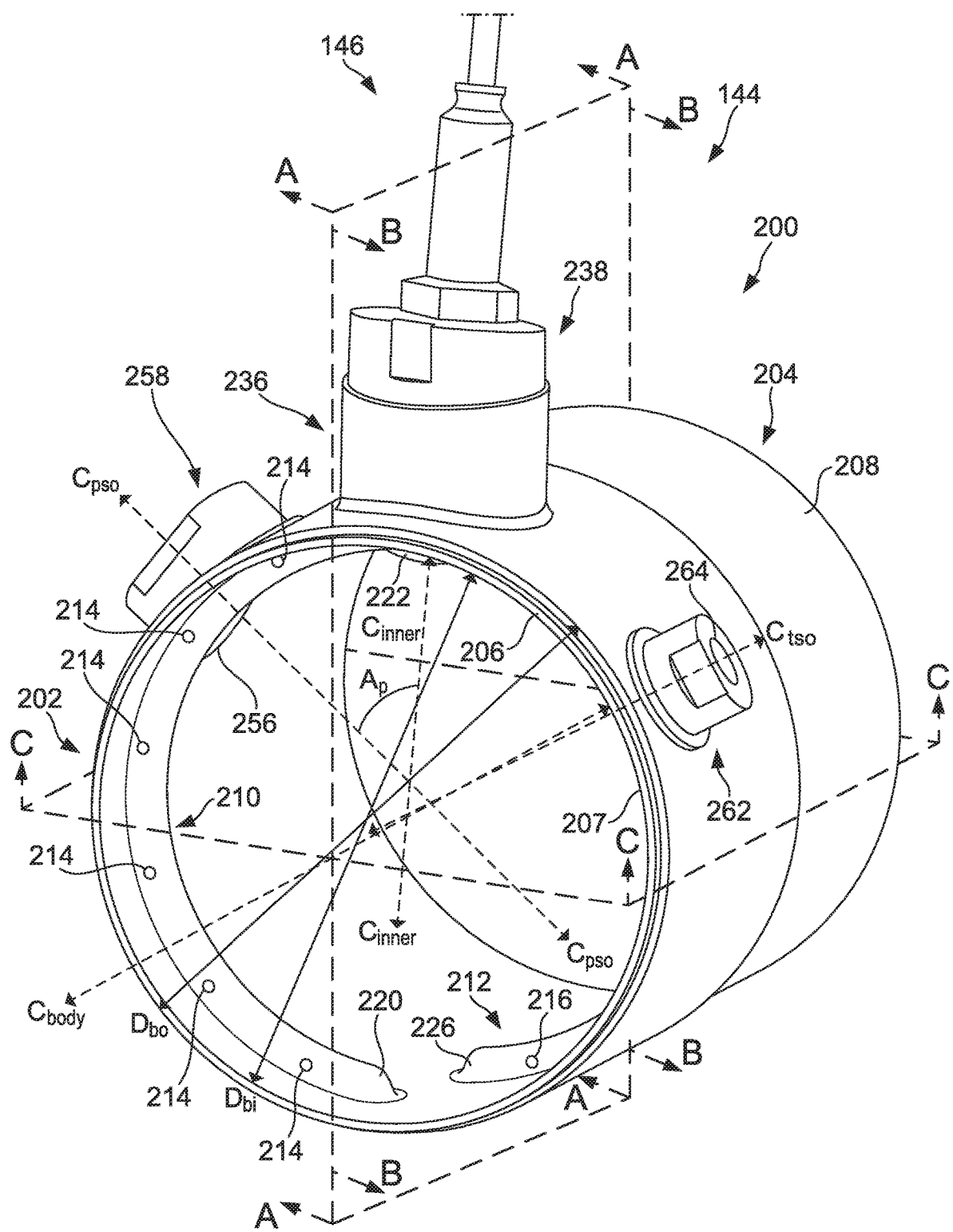
FIG. 2 is a perspective view of an example sampling assembly for an exhaust gas aftertreatment system.

It will be recognized that some or all of the Figures are schematic representations for purposes of illustration. The Figures are provided for the purpose of illustrating one or more implementations with the explicit understanding that they will not be used to limit the scope or the meaning of the claims.

DETAILED DESCRIPTION

Following below are more detailed descriptions of various concepts related to, and implementations of, methods, apparatuses, and for sampling exhaust gas in an exhaust gas aftertreatment system of an internal combustion engine. The various concepts introduced above and discussed in greater detail below may be implemented in any of a number of ways, as the described concepts are not limited to any particular manner of implementation. Examples of specific implementations and applications are provided primarily for illustrative purposes.

I. Overview

Internal combustion engines (e.g., diesel internal combustion engines, etc.) produce exhaust gas that contains constituents, such as $NO_x$, $N_2$, $CO_2$, and/or $H_2O$. In some applications, an engine monitors the various amount of these constituents. When the amount of a constituent is above or below a threshold, the internal combustion engine can, for example, alter performance of an exhaust gas aftertreatment system associated with the internal combustion engine (e.g., in order to reduce the amount of a constituent, etc.).

Monitoring of the exhaust gas may be achieved by sampling the exhaust gas within the exhaust gas aftertreatment system using various sensors. This sampling is performed using a sampler. Typical samplers extend into and across a pathway within which the exhaust gas flows. For example, some samplers include sampling tubes that extend across a diameter of the pathway within which the exhaust gas flows. As a result of extending across the pathway, these samplers may increase the backpressure experienced by the internal combustion engine and may increase the amount of noise in downstream exhaust gas, both of which may result in undesirable operation of the internal combustion engine.

Exhaust gas may contain liquid. Contact between liquid and a sensor may be undesirable. In order to account for liquid in exhaust gas, some samplers include water shields. These water shields may add increased cost, complexity, and manufacturing constraints to typical samplers. Additionally, these water shields may not consistently prevent contact between liquid and sensors.

A sampler, or the sensors contained in a sampler, may need to be installed in various orientations or positions depending on constraints associated with a particular application. For example, some applications require sensors to be positioned at a specific rotational location. As a result, it is important that samplers operate desirably at various rotational positions. Typical samplers that sample gas by extending across the pathway within which exhaust gas flows may be unable to perform consistently across various rotational positions. As a result, typical samplers may not operate desirably in some applications.

Implementations described herein are related to a sampling assembly that samples exhaust gas using samplers that protrude into, but do not extend across, a passage within which the exhaust gas flows. As a result, the sampling assembly described herein is capable of sampling exhaust gas without the increasing in backpressure and downstream noise caused by typical samplers.

Furthermore, the sampling assembly described herein includes various components, such as the samplers, a sampler channel collector, an outer bowl, and an inner bowl which cooperate to swirl the exhaust gas such that a sample can be obtained by a sensor near a center of the swirl. In this way and others, the transmission of liquid into the sensor can be mitigated or prevented.

Still further, the sampling assembly described herein facilitates clocking of sensors to accommodate various constraints associated with the sensors. For example, an outer bowl, an inner bowl, and a coupling may be arranged such that a center axis of the sensor does not intersect the inner bowl or the outer bowl, thereby facilitating consistent sampling of the exhaust gas at various rotational positions of the sensor.

Additionally, the sampling assembly described herein facilitates installation at various rotational orientations. For example, the samplers may be configured to provide the same flow of exhaust gas into an outer bowl regardless of the rotational orientation of the sampling assembly because of the configuration of the samplers.

II. Example Exhaust Gas Aftertreatment System

FIG. 1 depicts an exhaust gas aftertreatment system 100 having an example reductant delivery system 102 for an exhaust conduit system 104. The exhaust gas aftertreatment system 100 includes the reductant delivery system 102, a particulate filter (e.g., a diesel particulate filter (DPF)) 106, a decomposition chamber 108 (e.g., reactor, reactor pipe, etc.), and a SCR catalyst 110.

The DPF 106 is configured to remove particulate matter, such as soot, from exhaust gas flowing in the exhaust conduit system 104. The DPF 106 includes an inlet, where the exhaust gas is received, and an outlet, where the exhaust gas exits after having particulate matter substantially filtered from the exhaust gas and/or converting the particulate matter into carbon dioxide. In some implementations, the DPF 106 may be omitted.

The decomposition chamber 108 is configured to convert a reductant into ammonia. The reductant may be, for example, urea, diesel exhaust fluid (DEF), Adblue®, a urea water solution (UWS), an aqueous urea solution (e.g., AUS32, etc.), and other similar fluids. The decomposition chamber 108 includes an inlet fluidly coupled to (e.g., fluidly configured to communicate with, etc.) the DPF 106 to receive the exhaust gas containing $NO_x$ emissions and an outlet for the exhaust gas, $NO_x$ emissions, ammonia, and/or reductant to flow to the SCR catalyst 110.

The reductant delivery system 102 includes a dosing module 112 (e.g., doser, etc.) configured to dose the reductant into the decomposition chamber 108 (e.g., via an injector). The dosing module 112 is mounted to the decomposition chamber 108 such that the dosing module 112 may dose the reductant into the exhaust gas flowing in the exhaust conduit system 104. The dosing module 112 may include an insulator interposed between a portion of the dosing module 112 and the portion of the decomposition chamber 108 on which the dosing module 112 is mounted.

The dosing module 112 is fluidly coupled to a reductant source 114. The reductant source 114 may include multiple reductant sources 114. The reductant source 114 may be, for example, a diesel exhaust fluid tank containing Adblue®. A reductant pump 116 (e.g., supply unit, etc.) is used to pressurize the reductant from the reductant source 114 for delivery to the dosing module 112. In some embodiments, the reductant pump 116 is pressure controlled (e.g., controlled to obtain a target pressure, etc.). The reductant pump 116 includes a reductant filter 118. The reductant filter 118 filters (e.g., strains, etc.) the reductant prior to the reductant being provided to internal components (e.g., pistons, vanes, etc.) of the reductant pump 116. For example, the reductant filter 118 may inhibit or prevent the transmission of solids (e.g., solidified reductant, contaminants, etc.) to the internal components of the reductant pump 116. In this way, the reductant filter 118 may facilitate prolonged desirable operation of the reductant pump 116. In some embodiments, the reductant pump 116 is coupled to a chassis of a vehicle associated with the exhaust gas aftertreatment system 100.

The dosing module 112 includes at least one injector 120. Each injector 120 is configured to dose the reductant into the exhaust gas (e.g., within the decomposition chamber 108, etc.). In some embodiments, the reductant delivery system 102 also includes an air pump 122. In these embodiments, the air pump 122 draws air from an air source 124 (e.g., air intake, etc.) and through an air filter 126 disposed upstream of the air pump 122. Additionally, the air pump 122 provides the air to the dosing module 112 via a conduit. In these embodiments, the dosing module 112 is configured to mix the air and the reductant into an air-reductant mixture and to provide the air-reductant mixture into the decomposition chamber 108. In other embodiments, the reductant delivery system 102 does not include the air pump 122 or the air source 124. In such embodiments, the dosing module 112 is not configured to mix the reductant with air.

The dosing module 112 and the reductant pump 116 are also electrically or communicatively coupled to a reductant delivery system controller 128. The reductant delivery system controller 128 is configured to control the dosing module 112 to dose the reductant into the decomposition chamber 108. The reductant delivery system controller 128 may also be configured to control the reductant pump 116.

The reductant delivery system controller 128 includes a processing circuit 130. The processing circuit 130 includes a processor 132 and a memory 134. The processor 132 may include a microprocessor, an application-specific integrated circuit (ASIC), a field-programmable gate array (FPGA), etc., or combinations thereof. The memory 134 may include, but is not limited to, electronic, optical, magnetic, or any other storage or transmission device capable of providing a processor, ASIC, FPGA, etc. with program instructions. This memory 134 may include a memory chip, Electrically Erasable Programmable Read-Only Memory (EEPROM), Erasable Programmable Read Only Memory (EPROM), flash memory, or any other suitable memory from which the reductant delivery system controller 128 can read instructions. The instructions may include code from any suitable programming language. The memory 134 may include various modules that include instructions which are configured to be implemented by the processor 132.

In various embodiments, the reductant delivery system controller 128 is configured to communicate with a central controller 136 (e.g., engine control unit (ECU)), engine control module (ECM), etc.) of an internal combustion engine having the exhaust gas aftertreatment system 100. In some embodiments, the central controller 136 and the reductant delivery system controller 128 are integrated into a single controller.

In some embodiments, the central controller 136 is communicable with a display device (e.g., screen, monitor, touch screen, heads up display (HUD), indicator light, etc.). The display device may be configured to change state in response to receiving information from the central controller 136. For example, the display device may be configured to change between a static state (e.g., displaying a green light, displaying a "SYSTEM OK" message, etc.) and an alarm state (e.g., displaying a blinking red light, displaying a "SERVICE NEEDED" message, etc.) based on a communication from the central controller 136. By changing state, the display device may provide an indication to a user (e.g., operator, etc.) of a status (e.g., operation, in need of service, etc.) of the reductant delivery system 102.

The decomposition chamber 108 is located upstream of the SCR catalyst 110. As a result, the reductant is injected upstream of the SCR catalyst 110 such that the SCR catalyst 110 receives a mixture of the reductant and exhaust gas. The reductant droplets undergo the processes of evaporation, thermolysis, and hydrolysis to form non-$NO_x$ emissions (e.g., gaseous ammonia, etc.) within the exhaust conduit system 104.

The SCR catalyst 110 is configured to assist in the reduction of $NO_x$ emissions by accelerating a $NO_x$ reduction process between the ammonia and the $NO_x$ of the exhaust gas into diatomic nitrogen, water, and/or carbon dioxide. The SCR catalyst 110 includes an inlet fluidly coupled to the decomposition chamber 108 from which exhaust gas and reductant are received and an outlet fluidly coupled to an end of the exhaust conduit system 104.

The exhaust gas aftertreatment system 100 may further include an oxidation catalyst (e.g., a diesel oxidation catalyst (DOC)) fluidly coupled to the exhaust conduit system 104 (e.g., downstream of the SCR catalyst 110 or upstream of the DPF 106) to oxidize hydrocarbons and carbon monoxide in the exhaust gas.

In some implementations, the DPF 106 may be positioned downstream of the decomposition chamber 108. For instance, the DPF 106 and the SCR catalyst 110 may be combined into a single unit. In some implementations, the dosing module 112 may instead be positioned downstream of a turbocharger or upstream of a turbocharger.

In various embodiments, the exhaust gas aftertreatment system 100 also includes a mixing assembly 138 (e.g., mixer, multi-stage mixer, etc.). The mixing assembly 138 is disposed between a decomposition chamber upstream portion 140 and a decomposition chamber downstream portion 142. Together, the decomposition chamber upstream portion 140, the mixing assembly 138, and the decomposition chamber downstream portion 142, form the decomposition chamber 108. The dosing module 112 is coupled to the mixing assembly 138 and the injector 120 is configured to dose the reductant into the mixing assembly 138. As will be explained in more detail herein, the mixing assembly 138 functions to mix the exhaust gas received from the decomposition chamber upstream portion 140 with the reductant provided by the mixing assembly 138 and provide the decomposition chamber downstream portion 142 with exhaust gas that have been mixed with the reductant.

The exhaust gas aftertreatment system 100 also includes a sampling assembly 144. In various embodiments, the sampling assembly 144 is positioned downstream of the SCR catalyst 110. However, in other embodiments the sampling assembly 144 is additionally or alternatively positioned upstream of the SCR catalyst 110 (e.g., upstream of the DPF 106, downstream of the DPF 106 and upstream of the decomposition chamber 108, downstream of the decomposition chamber 108 and upstream of the SCR catalyst 110, etc.).

In various embodiments, the sampling assembly 144 includes a $NO_x$ sensor 146, a particulate sensor 148, and a temperature sensor 150. The $NO_x$ sensor 146 is configured to determine an amount (e.g., level, volume, etc.) of $NO_x$ in the exhaust gas flowing through the sampling assembly 144. The $NO_x$ sensor 146 may be, for example, a Continental 2.8 $NO_x$ sensor, a Continental 2.0 $NO_x$ sensor, or a Bosch 4.0 $NO_x$ sensor. The particulate sensor 148 is configured to determine an amount of particulates in the exhaust gas flowing through the sampling assembly 144. The temperature sensor 150 is configured to determine a temperature of the exhaust gas flowing through the sampling assembly 144. The $NO_x$ sensor 146, the particulate sensor 148, and the temperature sensor 150 are configured to communicate with the reductant delivery system controller 128. For example, an amount of $NO_x$ determined by the $NO_x$ sensor 146 may be provided to the reductant delivery system controller 128, an amount of particulates determined by the particulate sensor 148 may be provided to the reductant delivery system controller 128, and a temperature determined by the temperature sensor 150 may be provided to the reductant delivery system controller 128. In some implementations, various of the $NO_x$ sensor 146, the particulate sensor 148, and the temperature sensor 150 are omitted.

While the exhaust gas aftertreatment system 100 has been shown and described in the context of use with a diesel internal combustion engine, it is understood that the exhaust gas aftertreatment system 100 may be used with other internal combustion engines, such as gasoline internal combustion engines, hybrid internal combustion engines, propane internal combustion engines, and other similar internal combustion engines.

FIGS. 2-12 illustrate the sampling assembly 144 in greater detail according to various embodiments. As is explained in more detail herein, the sampling assembly 144 is configured to facilitate sampling of the exhaust gas flowing through the sampling assembly 144 such that an amount of a constituent, such as $NO_x$, in the exhaust gas can be determined by a sensor. As is also explained in more detail herein, the sampling assembly 144 is structured such that transmission of liquid (e.g., water, reductant, fluid etc.) to a sensor element of the sensor is substantially prohibited (e.g., such that the sensor element is substantially isolated from any liquid entering the sampling assembly 144, etc.). In some applications, a sensor can become undesirable when a sensor element of the sensor is exposed to liquid. Therefore, the sampling assembly 144 may be capable of being more desirable than other systems which do not substantially prohibit transmission of liquid to a sensor element of a sensor. The sampling assembly 144 includes a sampling assembly body 200 (e.g., frame, structure, etc.).

III. First Example Sampling Assembly

FIGS. 2-8 illustrate an example sampling assembly 144 with the sampling assembly body 200 according to various embodiments. The sampling assembly body 200 includes a sampling assembly body upstream end 202 and a sampling assembly body downstream end 204. The sampling assembly body upstream end 202 is configured to be coupled to (e.g., fastened to, welded to, clamped to, clamped to using a band clamp, etc.) an upstream exhaust conduit and the sampling assembly body downstream end 204 is configured to be coupled to (e.g., fastened to, welded to, clamped to, clamped to using a band clamp, etc.) a downstream exhaust conduit. The sampling assembly body upstream end 202 is configured to receive the exhaust gas (e.g., from a component of the exhaust gas aftertreatment system 100 that is upstream of the sampling assembly 144, etc.) and the sampling assembly body downstream end 204 is configured to provide the exhaust gas (e.g., to a component of the exhaust gas aftertreatment system 100 that is downstream of the sampling assembly 144, etc.).

The sampling assembly body 200 has (e.g., is centered on) a sampling assembly body center axis $C_{body}$. The sampling assembly body 200 is generally cylindrical and has a sampling assembly body outer diameter $D_{bo}$ and a sampling assembly body inner diameter $D_{bi}$. As will be explained in more detail herein, the sampling assembly body 200 includes samplers that protrude towards $C_{body}$. $D_{bi}$ is measured at a location that does not include these samplers. $D_{bi}$ may be, for example, 2 inches, 3 inches, 4 inches, 5, inches, 6 inches, or other similar values. $D_{bo}$ is larger than $D_{bi}$. For example, $D_{bo}$ may be 101%, 102%, 105%, 110%, or other similar percentages, of $D_{bi}$.

In various embodiments, $D_{bo}$ and $D_{bi}$ are substantially constant (e.g., +/−1%, +/−2%, +/−5%, etc.) from the sampling assembly body upstream end 202 to the sampling assembly body downstream end 204 (e.g., along the length of the sampling assembly body 200, etc.). In other embodiments, $D_{bo}$ and $D_{bi}$ vary (e.g., decrease, increase, alternatively increase and decrease, etc.) from the sampling assembly body upstream end 202 to the sampling assembly body downstream end 204.

The sampling assembly body 200 also includes a base body layer 206 (e.g., inner layer, first body layer, etc.) and a wrap body layer 208 (e.g., outer layer, second body layer, etc.). The base body layer 206 defines a passage 207 (e.g., cylindrical passage, cylindrical opening, etc.) within which the exhaust gas provided from the sampling assembly body upstream end 202 is conveyed to the sampling assembly body downstream end 204. The wrap body layer 208 is disposed on top of (e.g., overlaps, covers, etc.) the base body layer 206. The base body layer 206 interfaces with (e.g., contacts, etc.) the exhaust gas and the wrap body layer 208 is partially separated (e.g., isolated, etc.) from the exhaust gas base of the base body layer 206. As a result, the base body layer 206 is at least partially separated from an ambient environment (e.g., atmosphere, etc.) by the wrap body layer 208. In various embodiments, the wrap body layer 208 is wrapped (e.g., rolled, folded, coiled, etc.) onto the base body layer 206 such that the base body layer 206 is completely overlapped (e.g., covered, etc.) by the wrap body layer 208. In some embodiments, the wrap body layer 208 is wrapped onto only a portion of the base body layer 206 (e.g., such that a portion of the base body layer 206 is not covered by the wrap body layer 208, such that a portion of the base body layer 206 is exposed, etc.).

The base body layer 206 includes a first sampler 210 (e.g., sampling arc, sampling ring, etc.) and a second sampler 212 (e.g., sampling arc, sampling ring, etc.). Each of the first sampler 210 and the second sampler 212 extends circumferentially along the base body layer 206 (e.g., extend along a perimeter of the passage 207, etc.). In some embodiments, the first sampler 210 and second sampler 212 are formed by deforming (e.g., bending, etc.) the base body layer 206 (e.g., using a die, etc.). In these embodiments, exhaust gas flowing through the first sampler 210 and the second sampler 212 interfaces with the wrap body layer 208. In other embodiments, the first sampler 210 and second sampler 212 are separate structures that are coupled to the base body layer 206. For example, the first sampler 210 may be placed over the base body layer 206 and welded to the base body layer 206 during assembly of the sampling assembly body 200. In some of these embodiments, exhaust gas flowing through the first sampler 210 and the second sampler 212 does not interface with the wrap body layer 208 and instead only interfaces with the base body layer 206.

The first sampler 210 and the second sampler 212 are raised structures (e.g., relative to the portions of the base body layer 206 other than the first sampler 210 or the second sampler 212, etc.), such that the first sampler 210 and the second sampler 212 protrude into the passage defined by the sampling assembly body 200 and towards $C_{body}$. As a result, a portion (e.g., a portion near the base body layer 206, etc.) of the exhaust gas flowing into the sampling assembly body upstream end 202 flows against (e.g., contacts, etc.) the first sampler 210 and/or the second sampler 212.

Due to the unobtrusive location of the first sampler 210 and the second sampler 212, the sampling assembly 144 is capable of operating with a pressure drop (e.g., a difference between a pressure of the exhaust gas flowing into the sampling assembly body upstream end 202 and a pressure of the exhaust gas flowing out of sampling assembly body downstream end 204, etc.) that is low compared to other sampling devices, such as those that extend across a passage within which exhaust gas flows. For example, the pressure drop of the sampling assembly 144 may be substantially equal to 1 kilopascal (kPa). As utilized herein, a description of a first value being "substantially equal" to a second value describes the first value as being equal to the second value and the first value as being within 5%, inclusive, of the second value (e.g., the first value is equal to 105% of the second value, the first value is equal to 95% of the second value, etc.). In some applications, the pressure drop of the sampling assembly 144 may be substantially equal to less than 5 kPa, less than 3 kPa, less than 2 kPa, or less than 0.5 kPa. In various applications, the pressure drop is between 0.25 kPa and 2 kPa, inclusive. In this way, the sampling assembly 144 may be significantly more desirably than other sampling devices which produce significant pressure drops.

The first sampler 210 includes a plurality of first sampler apertures 214 (e.g., holes, openings, etc.) and the second sampler 212 includes a plurality of second sampler apertures 216 (e.g., holes, openings, etc.). As the exhaust gas flows from the sampling assembly body upstream end 202 to the sampling assembly body downstream end 204, a portion of the exhaust gas may flow through any of the first sampler apertures 214 and into the first sampler 210 and/or through any of the second sampler apertures 216 and into the second sampler 212.

After the exhaust gas flows through one of the first sampler apertures 214, the exhaust gas enters a first sampler channel 218 (e.g., void, gap, etc.) of the first sampler 210. The first sampler channel 218 is formed between the base body layer 206 and the wrap body layer 208. The first sampler channel 218 extends circumferentially from a first sampler first end 220 (e.g., terminal, etc.) to a first sampler second end 221 (e.g., terminal, etc.). Exhaust gas flows from the first sampler channel 218 into a sampler channel collector 222. In various embodiments, the first sampler second end 221 is located proximate to, or is contiguous with, the sampler channel collector 222. In other embodiments, the sampler channel collector 222 is located along a length of the first sampler channel 218, such as near a midpoint of the first sampler channel 218, such that the exhaust gas flows from each of the first sampler first end 220 and the first sampler second end 221 to the sampler channel collector 222. The flow of the exhaust gas is illustrated by solid arrows in FIG. 3. The base body layer 206 and the wrap body layer 208 interface about the first sampler first end 220 such that flow of the exhaust gas between the base body layer 206 and the wrap body layer 208 out of the first sampler first end 220, aside from flow through the first sampler channel 218, is substantially prohibited. Similarly, the base body layer 206 and the wrap body layer 208 interface about the first sampler second end 221 such that flow of the exhaust gas between the base body layer 206 and the wrap body layer 208 out of the first sampler second end 221, aside from flow through the first sampler channel 218, is substantially prohibited.

Similarly, after the exhaust gas flows through one of the second sampler apertures 216, the exhaust gas enters a second sampler channel 224 (e.g., void, gap, etc.) of the second sampler 212. The second sampler channel 224 is formed between the base body layer 206 and the wrap body layer 208. The second sampler channel 224 extends circumferentially from a second sampler first end 226 (e.g., terminal, etc.) to a second sampler second end 227. Exhaust gas flows from the second sampler channel 224 into the sampler channel collector 222. In various embodiments, the second sampler second end 227 is located proximate to, or is contiguous with, the sampler channel collector 222. In other embodiments, the sampler channel collector 222 is located along a length of the second sampler channel 224, such as near a midpoint of the second sampler channel 224, such that the exhaust gas flows from each of the second sampler first end 226 and the second sampler second end 227 to the sampler channel collector 222. The base body layer 206 and the wrap body layer 208 interface about the second sampler first end 226 such that flow of the exhaust gas between the base body layer 206 and the wrap body layer 208 out of the second sampler first end 226, aside from flow through the second sampler channel 224, is substantially prohibited. Similarly, the base body layer 206 and the wrap body layer 208 interface about the second sampler second end 227 such that flow of the exhaust gas between the base body layer 206 and the wrap body layer 208 out of the second sampler second end 227, aside from flow through the second sampler channel 224, is substantially prohibited.

In some embodiments, the first sampler 210 and the second sampler 212 are configured such that the exhaust gas can be sampled consistently (e.g., with negligible variation, etc.) regardless of the rotational orientation of the sampling assembly body 200. For example, the first sampler 210 and the second sampler 212 may be configured to receive a substantially equal flow of the exhaust gas regardless of the rotational orientation of the sampling assembly body 200. In some applications, the first sampler 210 and the second sampler 212 are identical (e.g., a quantity of the first sampler apertures 214 in the first sampler 210 is the same as a quantity of the second sampler apertures 216 in the second sampler 212, a flow rate at which the first sampler channel 218 provides the exhaust gas into the sampler channel collector 222 is the same as a flow rate at which the second sampler channel 224 provides the exhaust gas into the sampler channel collector 222, etc.). As is explained in more detail herein, the $NO_x$ sensor 146, the particulate sensor 148, and the temperature sensor 150 are each coupled to the sampling assembly body 200. In some applications, it may be desirable to rotate the sampling assembly body 200 to accommodate the $NO_x$ sensor 146, the particulate sensor 148, and/or the temperature sensor 150. By configuring the first sampler 210 and the second sampler 212 to sample the exhaust gas consistently regardless of the rotational orientation of the sampling assembly body 200, the sampling assembly body 200 can be rotated and installed to accommodate the $NO_x$ sensor 146, the particulate sensor 148, and/or the temperature sensor 150 (e.g., due to space constraints, due to wiring constraints, due to mounting constraints, etc.) without negatively impacting the desirability of the sampling assembly body 200. In contrast, other samplers may inconsistently sample the exhaust gas when rotated. As a result, these other samplers may be unable to desirably accommodate various sensors.

Liquid in the exhaust gas flowing through the first sampler channel 218 and through the second sampler channel 224 may contain liquid. The first sampler channel 218 and the second sampler channel 224 are each defined by a length from the first sampler first end 220 to the sampler channel collector 222 and from the second sampler first end 226 to the sampler channel collector 222, respectively. By increasing the length of the first sampler channel 218 and the length of the second sampler channel 224, the temperature of the exhaust gas within the first sampler channel 218 and of the exhaust gas within the second sampler channel 224 may be increased (e.g., due to prolonging the heating provided by the exhaust gas flowing across the first sampler 210 or the second sampler 212, etc.). As the exhaust gas is heated, any liquid contained within the exhaust gas may evaporate. As a result, increasing the length of the first sampler channel 218 or the length of the second sampler channel 224 can mitigate the transmission of liquid into the sampler channel collector 222.

In various embodiments, the first sampler channel 218 and the second sampler channel 224 are configured such that the first sampler first end 220 and the second sampler first end 226 are located at approximately the same radial location on the base body layer 206. In such embodiments, the sampling assembly body 200 may be installed such that the first sampler first end 220 and the second sampler first end 226 are located at approximately a lowest vertical location on the base body layer 206 (e.g., a location that is the closest to a surface along which a vehicle having the exhaust gas aftertreatment system 100 is traversing, etc.). In this way, any liquid in the first sampler channel 218 may flow downwards (e.g., due to gravity, etc.) within the first sampler channel 218 and collect within the first sampler first end 220 and any liquid in the second sampler channel 224 may flow downwards (e.g., due to gravity, etc.) within the second sampler channel 224 and collect within the second sampler first end 226. When collected in the first sampler first end 220 or the second sampler first end 226, the liquid may be heated by the exhaust gas flowing across the first sampler first end 220 or the second sampler first end 226 and evaporate.

The exhaust gas from the first sampler channel 218 and the exhaust gas from the second sampler channel 224 mix in the sampler channel collector 222. The sampler channel collector 222 is circular and arranged such that the first sampler channel 218 and the second sampler channel 224 flow into the sampler channel collector 222 tangentially to the sampler channel collector 222. In this sense, tangentially means that a center axis of the first sampler channel 218 is parallel to, and that may also be offset from (e.g., relative to $C_{inner}$, etc.), a tangent of the sampler channel collector 222 and that a center axis of the second sampler channel 224 is parallel to, and that may also be offset from, a tangent of the sampler channel collector 222. Specifically, the exhaust gas provided from the first sampler channel 218 is provided into the sampler channel collector 222 along a first axis that is parallel to, and that may also be offset from, a first tangent of the sampler channel collector 222 and the exhaust gas provided from the second sampler channel 224 is provided into the sampler channel collector 222 along a second axis that is parallel to, and that may also be offset from, a second tangent of the sampler channel collector 222. In various embodiments, the first axis and the second axis are parallel. In some embodiments, the first axis and the second axis are parallel and separated by a distance greater than a radius of the sampler channel collector 222. As a result of these arrangements, the exhaust gas flowing from the first sampler channel 218 and the second sampler channel 224 are caused to swirl within the sampler channel collector 222.

The sampler channel collector 222 includes a sampler channel collector opening 230 (e.g., hole, aperture, etc.). The sampler channel collector opening 230 may be centered on a center point of the sampler channel collector 222. In various embodiments, the sampler channel collector opening 230 has a center axis that is orthogonal to $C_{body}$.

The sampling assembly body 200 also includes an inner bowl 232 (e.g., tube, pipe, etc.). The inner bowl 232 extends through the sampler channel collector opening 230 and is coupled to the sampler channel collector 222 about the sampler channel collector opening 230 such that flow of the exhaust gas between the sampler channel collector 222 and the inner bowl 232 is substantially prohibited. The inner bowl 232 and the sampler channel collector 222 are arranged such that the exhaust gas provided from the first sampler channel 218 is provided into the sampler channel collector 222 along a first axis that is parallel to, and that may also be offset from, a first tangent that extends between the inner bowl and the sampler channel collector 222 and such that the exhaust gas provided from the second sampler channel 224 is provided into the sampler channel collector 222 along a second axis that is parallel to, and that may also be offset from, a second tangent that extends between the inner bowl and the sampler channel collector 222. In some embodiments, the inner bowl 232 includes a plurality of swirl vanes. Each of the swirl vanes functions to cause the exhaust gas flowing within the inner bowl 232 to swirl.

The inner bowl 232 is centered on an inner bowl center axis $C_{inner}$. In various embodiments, $C_{inner}$ is orthogonal to $C_{body}$. For example, the $C_{inner}$ may be orthogonal to and intersect $C_{body}$. In some embodiments, the sampler channel collector opening 230 is centered on the $C_{inner}$.

The wrap body layer 208 includes a wrap body layer bowl opening 234 (e.g., opening, hole, etc.). In various embodiments, a diameter of the wrap body layer bowl opening 234 is substantially equal to a diameter of the sampler channel collector 222. The wrap body layer bowl opening 234 is positioned over the sampler channel collector 222. The inner bowl extends through the wrap body layer bowl opening 234.

The sampling assembly body 200 also includes an outer bowl 236 (e.g., tube, pipe, etc.). The outer bowl 236 is centered on the $C_{inner}$. As a result, the outer bowl 236 and the inner bowl 232 are concentric. The outer bowl 236 extends through the wrap body layer bowl opening 234 and is coupled to the wrap body layer 208 about the wrap body layer bowl opening 234 such that flow of the exhaust gas between the outer bowl 236 and the wrap body layer bowl opening 234 is substantially prohibited. In some embodiments, the outer bowl 236 includes a plurality of swirl vanes. Each of the swirl vanes functions to cause the exhaust gas flowing within the outer bowl 236 to swirl.

The exhaust gas flowing from the first sampler channel 218 enters the sampler channel collector 222 tangentially to the sampler channel collector 222 and opposite to the exhaust gas flowing from the second sampler channel 224 which also enters the sampler channel collector 222. As a result, the exhaust gas within the sampler channel collector 222 is caused to swirl between the inner bowl 232 and the sampler channel collector 222 and between the inner bowl 232 and the outer bowl 236. This swirl creates a centrifugal force which causes any liquid in the exhaust gas to be propelled radially outwards and against the sampler channel collector 222 or the outer bowl 236. When against the sampler channel collector 222 or the outer bowl 236, the liquid may be exposed to additional heat and caused to evaporate.

The exhaust gas flowing through the sampler channel collector 222 flows around the inner bowl 232, upwards, and into the outer bowl 236 (e.g., between the inner bowl 232 and the outer bowl 236, etc.). The centrifugal force created by the first sampler channel 218, the second sampler channel 224, and the sampler channel collector 222 impedes the movement of liquid into the outer bowl 236. The outer bowl 236 is defined by an outer bowl height $H_{ob}$ from an outer edge of the wrap body layer 208 to a top edge of the outer bowl 236. In some embodiments, the $H_{ob}$ is substantially equal to 25 millimeters (mm). In various applications, the $H_{ob}$ is substantially equal to 10 mm-40 mm, inclusive.

The sampling assembly body 200 also includes a $NO_x$ sensor coupling 238 (e.g., joint, adapter, bushing, etc.). The $NO_x$ sensor coupling 238 extends through, and is coupled to, the outer bowl 236. In some embodiments, the $NO_x$ sensor coupling 238 is welded to the outer bowl 236. In other embodiments, the $NO_x$ sensor coupling 238 is threaded into the outer bowl 236. In still other embodiments, the $NO_x$ sensor coupling 238 is press fit into the outer bowl 236 (e.g., via a friction fit, etc.).

The $NO_x$ sensor coupling 238 interfaces with the outer bowl 236 such that flow of the exhaust gas between the $NO_x$ sensor coupling 238 and the outer bowl 236 is substantially prohibited. The exhaust gas flowing into the outer bowl 236 is prohibited from flowing out of sampling assembly body 200, in part, via the $NO_x$ sensor coupling 238. As the exhaust gas flows into the outer bowl 236, the exhaust gas flows radially outward and against the $NO_x$ sensor coupling 238.

The $NO_x$ sensor coupling 238 includes a $NO_x$ sensor coupling opening 240 (e.g., hole, aperture, etc.). The $NO_x$ sensor coupling opening 240 is configured to receive the $NO_x$ sensor 146. The $NO_x$ sensor coupling opening 240 is centered on a $NO_x$ sensor coupling opening center axis $C_{NOx}$. The $C_{NOx}$ intersects the $C_{inner}$. In this way, the exhaust gas provided to the $NO_x$ sensor 146 may be provided from a low pressure zone at a center, or near the center, of a swirl created by the outer bowl 236 and/or the inner bowl 232.

In various embodiments, the $C_{NOx}$ is offset by a $NO_x$ sensor offset angle $A_{NOx}$ from the $C_{inner}$ in a plane along which the $C_{NOx}$ and the $C_{inner}$ are disposed. In various applications, the $A_{NOx}$ may be substantially equal to 15°, 12.5°, 12.15°, or other similar values. In various embodiments, the $C_{NOx}$ intersects $C_{body}$. In various applications, the $A_{NOx}$ is substantially equal to 10°-30°, inclusive.

The $NO_x$ sensor coupling 238 facilitates clocking (e.g., rotation, rotational repositioning, etc.) of the $NO_x$ sensor 146 relative to the outer bowl 236. Specifically, the $NO_x$ sensor coupling 238 is configured to be coupled to the outer bowl 236 in a plurality of rotational positions. These rotational positions may include any number of rotational positions between no rotation of the NOx sensor coupling 238 relative to the outer bowl 236 (e.g., 0°, etc.) and one full rotation of the NOx sensor coupling 238 relative to the outer bowl 236 (e.g., 360°, etc.). In some examples, these rotational positions include a first rotational position (e.g., 0°, etc.), a second rotational position (e.g., 90°, 110°, 150°, 200°, 325°, 350°, etc.) separated from the first rotational position by at least 90°, a third rotational position (e.g., 190°, 210°, 320°, 340°, etc.) separated from the first rotational position by at least 180°, and a fourth rotational position (e.g., 315°, 370°, etc.) separated from the first rotational position by at least 270°. This enables the $NO_x$ sensor coupling 238 to be rotated (e.g., using a clamp, using a pliers, using a wrench, etc.) relative to the inner bowl 232 such that the sampling assembly 144 is tailored for a target application. This may facilitate positioning of the $NO_x$ sensor 146 in a target orientation that is desirable for a target application (e.g., such that the $NO_x$ sensor 146 fits within a space claim associated with a target application, etc.).

The sampling assembly body 200 is configured to enable to NOx sensor 146 to sample the exhaust gas consistently regardless of the rotational position of the $NO_x$ sensor 146. Specifically, changing the rotational position of the $NO_x$ sensor 146 merely causes a rotation of the $NO_x$ sensor 146 relative to the inner bowl 232 (e.g., within the inner bowl 232, etc.). However, the sampler channel collector 222, the outer bowl 236, the inner bowl 232, and the $NO_x$ sensor coupling 238 cooperate to enable a flow of the exhaust gas into the $NO_x$ sensor 146 that is substantially the same at any rotational position of the $NO_x$ sensor. In contrast to the sampling assembly body 200, other samplers, such as those with a sampling tube protruding into the exhaust gas, may not be able to consistently sample an exhaust gas at any rotational position of a sensor.

As the exhaust gas flows against the $NO_x$ sensor coupling 238, the exhaust gas is redirected downwards and flows towards an outer sensor shield 242 (e.g., cover, etc.) of the $NO_x$ sensor 146. A portion of the exhaust gas enters the outer sensor shield 242 via one or more outer sensor shield openings 244 (e.g., apertures, holes, etc.) while a remaining portion of the exhaust gas continues to flows into the inner bowl 232 and downwards past the outer sensor shield 242.

The outer sensor shield openings 244 each have a diameter. This diameter may be selected so as to impede the flow of liquid through the outer sensor shield openings 244 (e.g., the diameter of the outer sensor shield openings 244 may be smaller than a diameter of an undesirable amount of liquid, etc.). In some applications, the diameter of each of the outer sensor shield openings 244 is 0.015625 inches, 0.01 inches, 0.001 inches, 0.005 inches, or other similar values.

The portion of the exhaust gas that flows through the outer sensor shield openings 244 flows against an inner sensor shield 246 (e.g., cover, etc.). An outer sensor shield wall 248 (e.g., barrier, etc.) is coupled to the outer sensor shield 242 and the inner sensor shield 246 such that flow between the outer sensor shield wall 248 and the outer sensor shield 242 is substantially prohibited and flow between the outer sensor shield wall 248 and the inner sensor shield 246 is substantially prohibited. The outer sensor shield 242 and the inner sensor shield 246 cooperatively define an annular cavity (e.g., void, etc.) therebetween. The exhaust gas within this annular cavity is directed upwards (e.g., due to the flow of the exhaust gas through the outer sensor shield openings 244, etc.) and enters the inner sensor shield 246 via one or more inner sensor shield openings 250 (e.g., apertures, holes, etc.).

Liquid in the exhaust gas in the annular cavity defined between the outer sensor shield 242 and the inner sensor shield 246 may collect on the outer sensor shield wall 248 (e.g., between the outer sensor shield 242, the inner sensor shield 246, and the outer sensor shield wall 248, etc.) due to gravity.

Similar to the outer sensor shield openings 244, the inner sensor shield openings 250 each have a diameter. This diameter may be selected so as to impede the flow of liquid through the inner sensor shield openings 250 (e.g., the diameter of the inner sensor shield openings 250 may be smaller than a diameter of an undesirable amount of liquid, etc.). In some applications, the diameter of each of the inner sensor shield openings 250 is 0.015625 inches, 0.01 inches, 0.001 inches, 0.005 inches, or other similar values.

The sampling assembly body 200 is capable of mitigating the transmission of liquid into the inner sensor shield 246 without the use of a separate water shield (e.g., additional component, etc.) as may be used in other samplers. As a result, the sampling assembly body 200 is capable of being produced more quickly (e.g., the sampling assembly body 200 includes less components, the sampling assembly body 200 is more readily scalable, etc.) and less expensively than other samplers. Additionally, the sampling assembly body 200 is capable of sampling the exhaust gas without creating noise in, or increasing the backpressure of, the flow of exhaust gas because a separate water shield, as used in other samplers, is not used in the sampling assembly body 200.

The portion of the exhaust gas that flows through the inner sensor shield openings 250 flows around a sensor element 252 (e.g., $NO_x$ sensor element, etc.). The sensor element 252 is configured to determine the amount of $NO_x$ in the exhaust gas. The exhaust gas flows within the inner sensor shield around the sensor element 252 and downwards towards an inner sensor shield outlet 254 (e.g., aperture, hole, etc.). The exhaust gas then flows through the inner sensor shield outlet 254 and into the inner bowl 232.

The exhaust gas that flows between the inner bowl 232 and the outer sensor shield 242 is drawn downwards, out of the inner bowl 232, and into the passage defined by the base body layer 206 (e.g., due to a vacuum created by the flow of the exhaust gas through the passage defined by the base body layer 206, etc.). A pressure differential between a pressure of the exhaust gas within the inner bowl 232 and a pressure of the exhaust gas within the passage defined by the base body layer 206 substantially prevents backflow of the exhaust gas into the inner bowl 232 (e.g., from the passage defined by the base body layer 206 into the inner bowl 232 and into the outer bowl 236, etc.).

The sampling assembly body 200 also includes a particulate sensor opening 256 (e.g., opening, hole, etc.). The particulate sensor opening 256 extends through the base body layer 206 or through the base body layer 206 and the wrap body layer 208. In various embodiments, the particulate sensor opening 256 is positioned downstream of the first sampler 210 and/or second sampler 212. The particulate sensor opening 256 is centered on a particulate sensor opening center axis $C_{pso}$. In various embodiments, the $C_{pso}$ is angularly offset by a particulate sensor offset angle $A_p$ relative to the $C_{inner}$. In various applications, the $A_p$ may be substantially equal to 50°, 55°, 60°, or other similar values. In various embodiments, the $C_{pso}$ intersects $C_{body}$. In various applications, the $A_p$ is substantially equal to 40°-70°, inclusive.

The sampling assembly body 200 also includes a particulate sensor coupling 258 (e.g., joint, adapter, bushing, etc.). The particulate sensor coupling 258 is coupled to the wrap body layer 208 about the particulate sensor opening 256 or the base body layer 206 about the particulate sensor opening 256.

The particulate sensor coupling 258 includes a particulate sensor coupling opening 260 (e.g., hole, aperture, etc.). The particulate sensor coupling opening 260 is configured to receive the particulate sensor 148. The particulate sensor coupling opening 260 may be centered on the $C_{pso}$ or another axis.

The sampling assembly body 200 also includes a temperature sensor opening (e.g., opening, hole, etc.) (not shown). The temperature sensor opening extends through the base body layer 206 or through the base body layer 206 and the wrap body layer 208. In various embodiments, the temperature sensor opening is positioned upstream of the first sampler 210 and/or second sampler 212. The temperature sensor opening is centered on a temperature sensor opening center axis $C_{tso}$. In various embodiments, $C_{tso}$ is angularly offset by a temperature sensor offset angle $A_t$ relative to the $C_{inner}$. In various applications, the $A_t$ may be substantially equal to 55°, 60°, 65°, or other similar values. In various embodiments, $C_{tso}$ intersects $C_{body}$. In various applications, the $A_t$ is substantially equal to 40°-70°, inclusive.

The sampling assembly body 200 also includes a temperature sensor coupling 262 (e.g., joint, adapter, bushing, etc.). The temperature sensor coupling 262 is coupled to the wrap body layer 208 about the temperature sensor opening or the base body layer 206 about the temperature sensor opening.

The temperature sensor coupling 262 includes a temperature sensor coupling opening 264 (e.g., hole, aperture, etc.). The temperature sensor coupling opening 264 is configured to receive the temperature sensor 150. The temperature sensor coupling opening 264 may be centered on $C_{tso}$ or another axis.

In various embodiments the temperature sensor opening is upstream of the sampler channel collector opening 230 and the particulate sensor opening 256 is downstream of the sampler channel collector opening 230. As a result, $C_{tso}$ is offset a temperature sensor length offset $L_{tso}$ from the $C_{inner}$ (e.g., towards the sampling assembly body upstream end 202, etc.) and the $C_{pso}$ is offset a particulate sensor length offset $L_{pso}$ (e.g., towards the sampling assembly body downstream end 204, etc.) from the $C_{inner}$. In various applications, the $L_{tso}$ may be substantially equal to 13 mm, 14 mm, 15 mm, or other similar values. In various applications, the $L_{tso}$ is substantially equal to 10 mm-20 mm, inclusive. In various applications, the $L_{pso}$ may be substantially equal to 13 mm, 14 mm, 15 mm, or other similar values. In various embodiments, the $L_{tso}$ is equal to the $L_{pso}$. In various applications, the $L_{pso}$ is substantially equal to 10 mm-20 mm, inclusive.

The temperature sensor opening is defined by a temperature sensor opening radius $r_{tso}$ and the particulate sensor opening 256 is defined by a particulate sensor opening radius $r_{pso}$. The temperature sensor opening, the particulate sensor opening 256, and the sampler channel collector opening 230 are disposed such that a total length T between an upstream edge of the temperature sensor opening and a downstream edge of the particulate sensor opening 256 is determined by $$r_{tso} + r_{pso} + L_{tso} + L_{pso} = T \tag{1}$$

calculating the sum of the rtso, the rpso, the Ltso, and the Lpso. In various applications, the T may be substantially equal to 60 mm, 62 mm, 64 mm, or other similar values. In various applications, the T is substantially equal to 50 mm-70 mm, inclusive.

In various embodiments, the first sampler 210 has a cross-section that is partially circular (e.g., along a plane that intersects $C_{body}$, etc.). In these embodiments, the first sampler 210 is defined by a first sampler diameter $d_{fs}$. In various applications, the $d_{fs}$ may be substantially equal to 9 mm, 10 mm, 11 mm, 12 mm, 13 mm, 14 mm, or other similar values. In various applications, the $d_{fs}$ is substantially equal to 5 mm-20 mm, inclusive.

In various embodiments, the second sampler 212 has a cross-section that is partially circular. In these embodiments, the second sampler 212 is defined by a second sampler diameter $d_{ss}$. In various applications, the $d_{ss}$ may be substantially equal to 9 mm, 10 mm, 11 mm, 12 mm, 13 mm, 14 mm, or other similar values. In some embodiments, the first sampler 210 has a cross-section that is partially circular and the second sampler 212 has a cross-section that is partially circular. In some of these embodiments, the $d_{fs}$ is equal to the $d_{ss}$. In various applications, the $d_{ss}$ is substantially equal to 5 mm-20 mm, inclusive.

In various embodiments, the first sampler apertures 214 are each circular and defined by a first sampler aperture diameter $d_{fsa}$. In various applications, the $d_{fsa}$ may be substantially equal to 1 mm, 1.5 mm, 2 mm, 2.5 mm, 3 mm, 3.5 mm, or other similar values. In various applications, the $d_{fsa}$ is substantially equal to 0.25 mm-5 mm, inclusive. The $d_{fsa}$ for each of the first sampler apertures 214 may be the same for all of the first sampler apertures 214 or may be different for some of the first sampler apertures 214.

In various embodiments, the second sampler apertures 216 are each circular and defined by a second sampler aperture diameter $d_{ssa}$. In various applications, the $d_{ssa}$ may be substantially equal to 1 mm, 1.5 mm, 2 mm, 2.5 mm, 3 mm, 3.5 mm, or other similar values. In various applications, the $d_{ssa}$ is substantially equal to 0.25 mm-5 mm, inclusive. The $d_{ssa}$ for each of the second sampler apertures 216 may be the same for all of the second sampler apertures 216 or may be different for some of the second sampler apertures 216. In some embodiments, the $d_{fsa}$ for some or all of the first sampler apertures 214 is equal to the $d_{ssa}$ for some or all of the second sampler apertures 216.

The outer bowl 236 is defined by an outer bowl inner diameter $d_{obi}$. In various embodiments, the $d_{obi}$ is constant along the $H_{ob}$. In other embodiments, the $d_{obi}$ varies (e.g., gradually increases, gradually decreases, etc.) along the $H_{ob}$. In various applications, the $d_{obi}$ may be substantially equal to 20 mm, 25 mm, 30 mm, 35 mm, 40 mm, 45 mm, or other similar values. In various applications, the $d_{obi}$ is substantially equal to 15 mm-50 mm, inclusive. In various applications, the $H_{ob}$ may be substantially equal to 15 mm, 20 mm, 25 mm, 30 mm, 35 mm, or other similar values. In various applications, the $H_{ob}$ is substantially equal to 5 mm-45 mm, inclusive.

The inner bowl 232 is defined by an inner bowl inner diameter dam and an inner bowl height $H_{ib}$. In various embodiments, the $d_{ibi}$ is constant along the $H_{ib}$. In other embodiments, the $d_{ibi}$ varies (e.g., gradually increases, gradually decreases, etc.) along the $H_{ib}$. In various applications, the dam may be substantially equal to 5 mm, 10 mm, 15 mm, 20 mm, 25 mm, or other similar values. In various applications, the dam is substantially equal to 2 mm-35 mm, inclusive.

The sampling assembly body 200 is also defined by a shield height $H_s$ between an inner bowl top edge 266 of the inner bowl 232 and the inner sensor shield outlet 254. The inner bowl top edge 266 defines an inlet into the inner bowl 232. In some embodiments, the $H_s$ is negative. In these embodiments, the outer sensor shield 242 extends into the inner bowl 232. In other embodiments, the $H_s$ is positive. In these embodiments, the outer sensor shield 242 is not positioned within the inner bowl 232 and is instead positioned above the inner bowl 232. In various applications, the $H_s$ may be substantially equal to −15 mm, −10 mm, −5 mm, −1 mm, 0 mm, 1 mm, 2 mm, 3 mm, 4 mm, 5 mm, 6 mm, 10 mm, or other similar values. In various applications, the $H_s$ is substantially equal to −20 mm-30 mm, inclusive.

The first sampler 210 and the second sampler 212 are each capable of being variously configured such that the sampling assembly body 200 is tailored for a target application. The first sampler first end 220 is defined by a first sampler offset angle $A_{fs}$ relative to the $C_{inner}$, a first sampler axial length $K_{fs}$ from the $C_{inner}$ along an axis parallel to $C_{body}$, and a first sampler circumferential length $L_{fs}$ from the sampler channel collector 222 to the first sampler first end 220 along a central axis $C_{fs}$ of the first sampler channel 218. Similarly, the second sampler first end 226 is defined by a second sampler offset angle $A_{cs}$ relative to the $C_{inner}$, a second sampler axial length $K_{ss}$ from the $C_{inner}$ along an axis parallel to $C_{body}$, and a second sampler circumferential length $L_{ss}$ from the sampler channel collector 222 to the second sampler first end 226 along a central axis $C_{ss}$ of the second sampler channel 224. By varying the $A_{fs}$, the $A_{cs}$, the $K_{fs}$, the $K_{ss}$, the $L_{fs}$, and the $L_{ss}$ the sampling assembly body 200 may be tailored for a target application. In some embodiments, the $L_{ss}$ is substantially equal to the $L_{fs}$. In various applications, the $K_{fs}$ is substantially equal to 0-13 mm, inclusive. In various applications, the $A_{fs}$ is substantially equal to 0°-15°, inclusive. In various applications, the $A_{cs}$ is substantially equal to 0°-15°, inclusive.

The first sampler 210 may include various numbers and configurations of the first sampler apertures 214. Each of the first sampler apertures 214 is defined by a first aperture distance $T_{fsa}$ from the first sampler first end 220. The $T_{fsa}$ may be different for each of the first sampler apertures 214 (e.g., where a number of the first sampler apertures 214 are spaced along the $C_{fs}$, etc.) and may be the same for a number of the first sampler apertures 214 (e.g., where one first sampler aperture 214 is located on an upstream portion of the first sampler 210 and another first sampler aperture 214 is located on a downstream portion of the first sampler 210, etc.). In various applications, the $T_{fsa}$ is substantially equal to 0-20 mm, inclusive.

Additionally, each of the first sampler apertures 214 may be located on an upstream portion of the first sampler 210 (e.g., proximate the sampling assembly body upstream end 202, etc.), a downstream portion of the first sampler 210 (e.g., proximate the sampling assembly body downstream end 204, etc.), or an inner portion of the first sampler 210 (e.g., between the upstream portion of the first sampler 210 and the downstream portion of the first sampler 210, etc.). By locating the first sampler aperture 214 on an upstream portion of the first sampler 210, momentum of the exhaust gas may be harnessed in propelling the exhaust gas into the first sampler channel 218. By locating the first sampler aperture 214 on a downstream portion of the first sampler 210 or an inner portion of the first sampler 210, pressure of the exhaust gas may be harnessed (e.g., rather than momentum, etc.) in propelling the exhaust gas into the first sampler channel 218.

The second sampler 212 may include various numbers and configurations of the second sampler apertures 216. Each of the second sampler apertures 216 is defined by a second aperture distance $T_{ssa}$ from the second sampler first end 226. The $T_{ssa}$ may be different for each of the second sampler apertures 216 (e.g., where a number of the second sampler apertures 216 are spaced along the $C_{ss}$, etc.) and may be the same for a number of the second sampler apertures 216 (e.g., where one second sampler aperture 216 is located on an upstream portion of the second sampler 212 and another second sampler aperture 216 is located on a downstream portion of the second sampler 212, etc.). In various applications, the $T_{ssa}$ is substantially equal to 0-20 mm, inclusive.

Additionally, each of the second sampler apertures 216 may be located on an upstream portion of the second sampler 212 (e.g., proximate the sampling assembly body upstream end 202, etc.), a downstream portion of the second sampler 212 (e.g., proximate the sampling assembly body downstream end 204, etc.), or an inner portion of the second sampler 212 (e.g., between the upstream portion of the second sampler 212 and the downstream portion of the second sampler 212, etc.). By locating the second sampler aperture 216 on an upstream portion of the second sampler 212, momentum of the exhaust gas may be harnessed in propelling the exhaust gas into the second sampler channel 224. By locating the second sampler aperture 216 on a downstream portion of the second sampler 212 or an inner portion of the second sampler 212, pressure of the exhaust gas may be harnessed (e.g., rather than momentum, etc.) in propelling the exhaust gas into the second sampler channel 224.

In various embodiments, the $A_{fs}$ is substantially equal to the $A_{cs}$. However, in some applications the $A_{fs}$ is greater than the $A_{cs}$ or the $A_{fs}$ is less than the $A_{cs}$.

In various embodiments, the $K_{fs}$ is negative (e.g., the first sampler first end 220 is between the $C_{inner}$ and the sampling assembly body upstream end 202 and the $K_{ss}$ is positive (e.g., the second sampler first end 226 is between the $C_{inner}$ and the sampling assembly body downstream end 204. However, in some applications, the $K_{fs}$ and the $K_{ss}$ are each negative or the $K_{fs}$ and the $K_{ss}$ are each positive.

In various embodiments, the $C_{fs}$ is substantially equal to the $C_{ss}$. However, in some applications the $C_{fs}$ is greater than the $C_{ss}$ or the $C_{fs}$ is less than the $C_{ss}$.

In some embodiments, the sampling assembly body 200 includes thermal insulation that is positioned to provide thermal insulation (e.g., to reduce heat transfer from the exhaust gas to atmosphere within the sampling assembly body 200, etc.) to any combination of the first sampler channel 218, the second sampler channel 224, the sampler channel collector 222, the outer bowl 236, the inner bowl 232, or the $NO_x$ sensor coupling 236. The thermal insulation may function to increase the temperature of any combination of the first sampler channel 218, the second sampler channel 224, the sampler channel collector 222, the outer bowl 236, the inner bowl 232, or the $NO_x$ sensor coupling 236 which may mitigate the transmission of liquid into the $NO_x$ sensor 146.

While the sampling assembly body 200 is shown and described as including the first sampler channel 218 and the second sampler channel 224, it is understood that the sampling assembly body 200 may include only the first sampler channel 218 or only the second sampler channel 224 in some embodiments. Similarly, it is understood that the sampling assembly body 200 may include additional sampler channels (e.g., two additional sampler channels, etc.) similar to the first sampler channel 218 or the second sampler channel 224.

While the inner bowl 232 and the outer bowl 236 are each shown and described as being cylindrical, it is understood that the inner bowl 232 and the outer bowl 236 may be oval-shaped, elliptical, polygonal, or otherwise similarly shaped such that the sampling assembly body 200 is tailored for a target application. Furthermore, it is understood that an inner surface of the inner bowl 232 may have a shape (e.g., cylindrical, etc.) that is different from a shape of an outer surface of the inner bowl 232 (e.g., elliptical, etc.) and that an inner surface of the outer bowl 236 may have a shape (e.g., elliptical, etc.) that is different from a shape of an outer surface of the outer bowl 236 (e.g., square, etc.).

IV. Second Example Sampling Assembly

Figure 9:
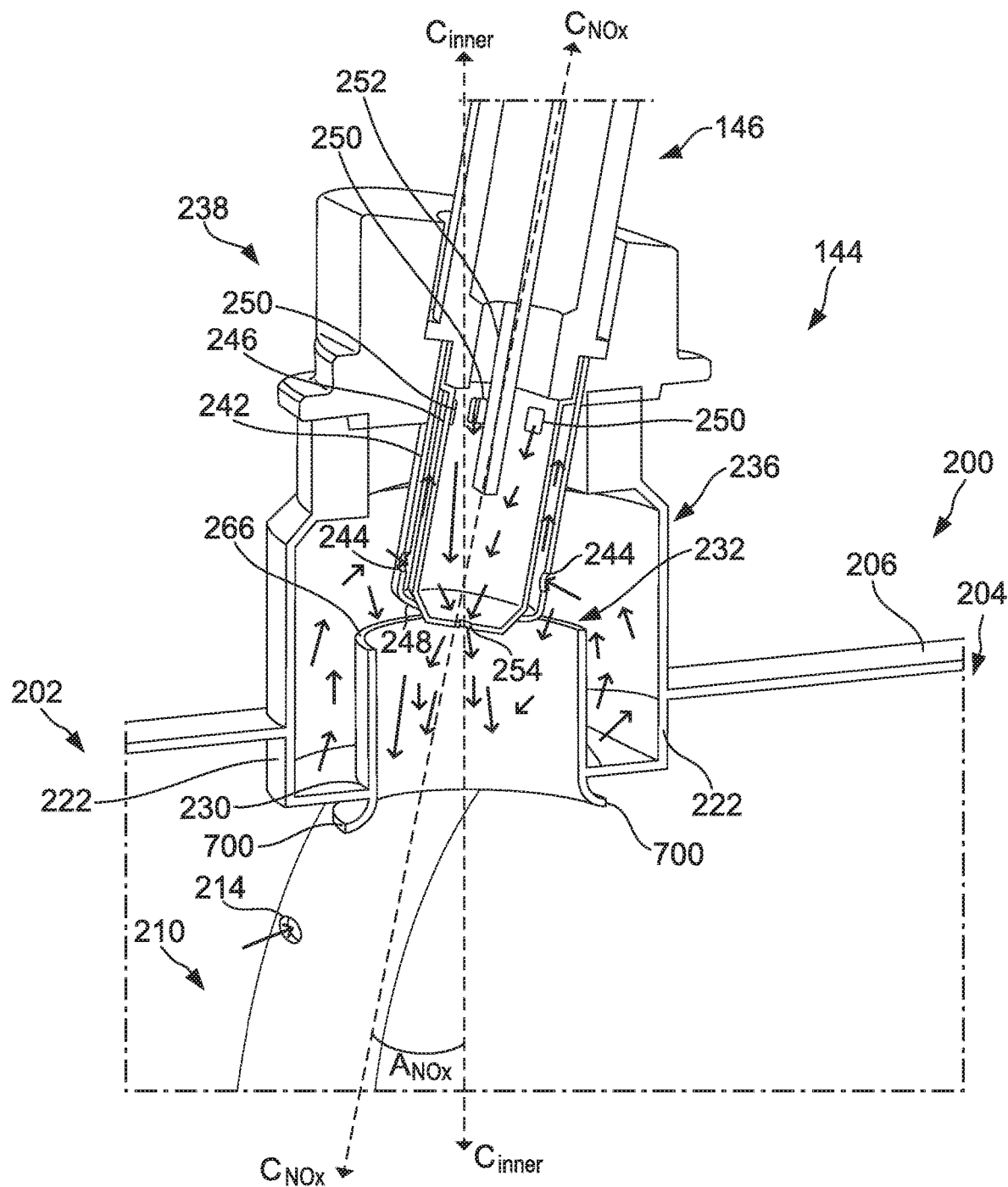
FIG. 9 is a detailed cross-sectional view of another example sampling assembly for an exhaust gas aftertreatment system.
Figure 10:
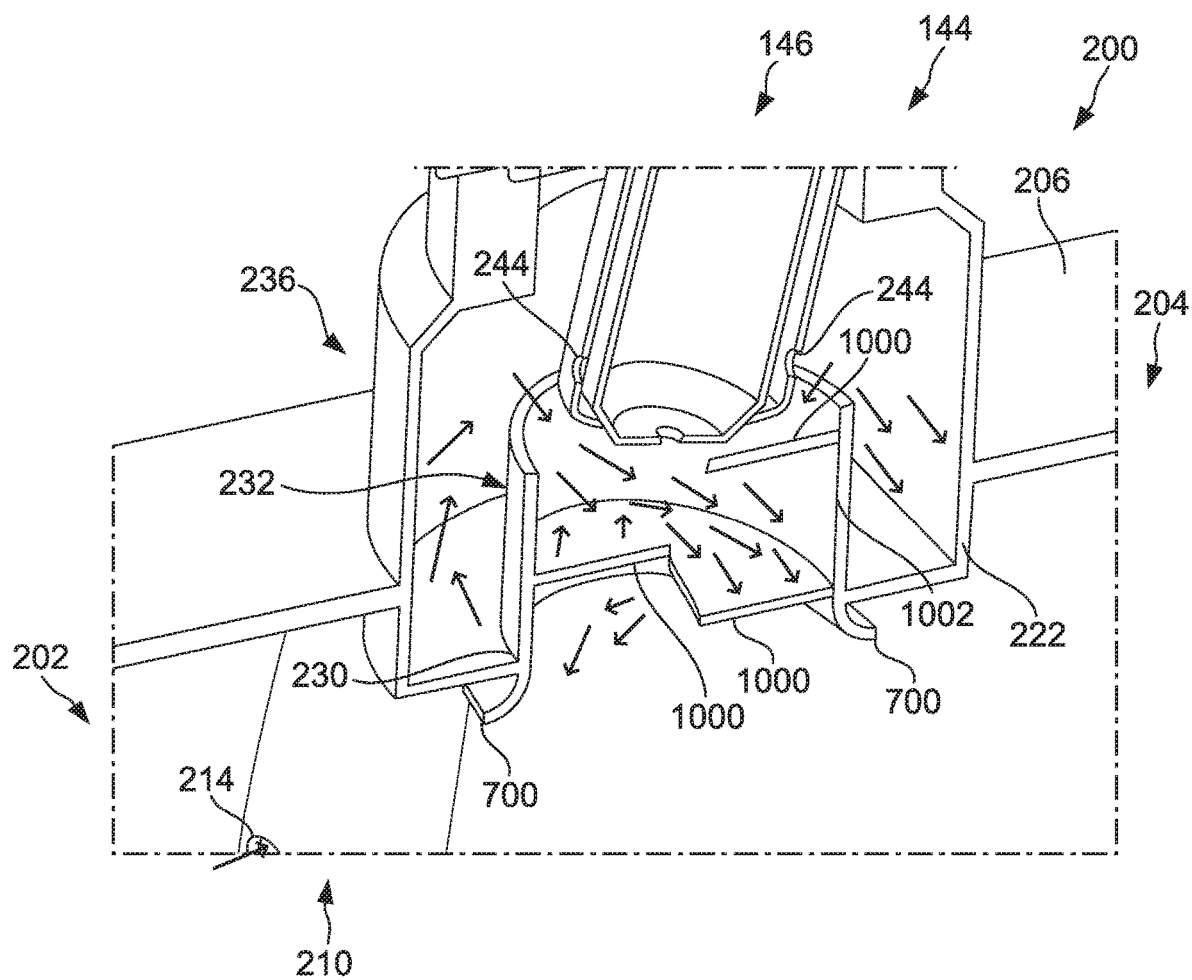
FIG. 10 is a detailed cross-sectional view of the example sampling assembly shown in FIG. 9 in some embodiments.

FIGS. 9 and 10 illustrate an example sampling assembly 144 with the sampling assembly body 200 according to various embodiments. The foregoing description of the sampling assembly 144 with respect to FIGS. 2-8 similarly applies to the sampling assembly 144 illustrated in FIGS. 9 and 10.

The sampling assembly body 200 is configured such that the sampler channel collector 222 is a portion of the outer bowl 236 (e.g., the sampler channel collector 222 is structurally integrated with the outer bowl 236, etc.). A portion of the outer bowl 236 is located outside of (e.g., external to, etc.) the base body layer 206, a portion of the outer bowl 236 extends through the base body layer 206, and a portion of the outer bowl 236, the sampler channel collector 222, is located within the base body layer 206. This arrangement of the outer bowl 236 and the sampler channel collector 222 may eliminate the need for the wrap body layer 208, thereby decreasing the cost of the sampling assembly body.

Figure 3:
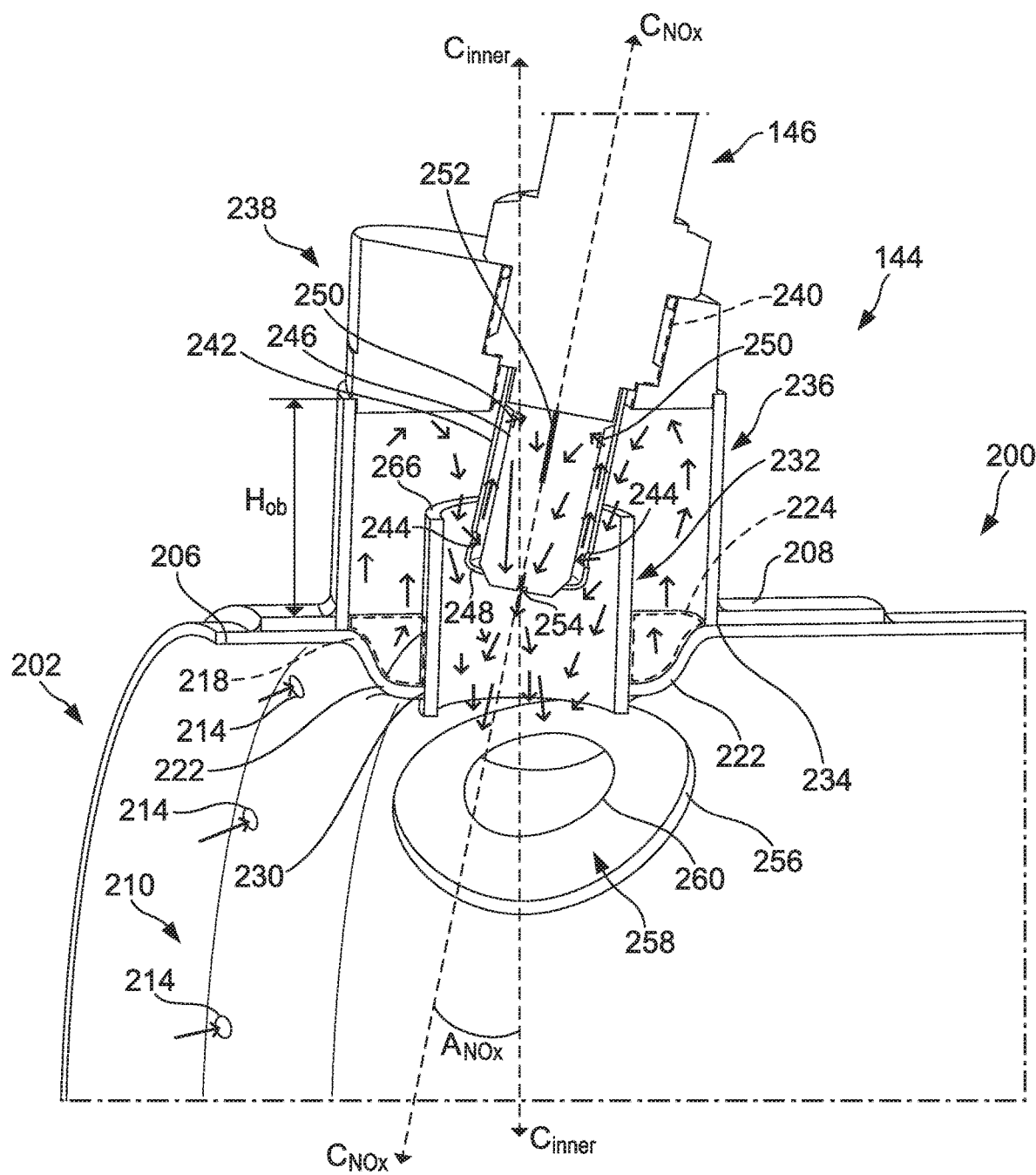
FIG. 3 is a detailed cross-sectional view of the example sampling assembly shown in FIG. 2, taken along plane A-A.
Figure 4:
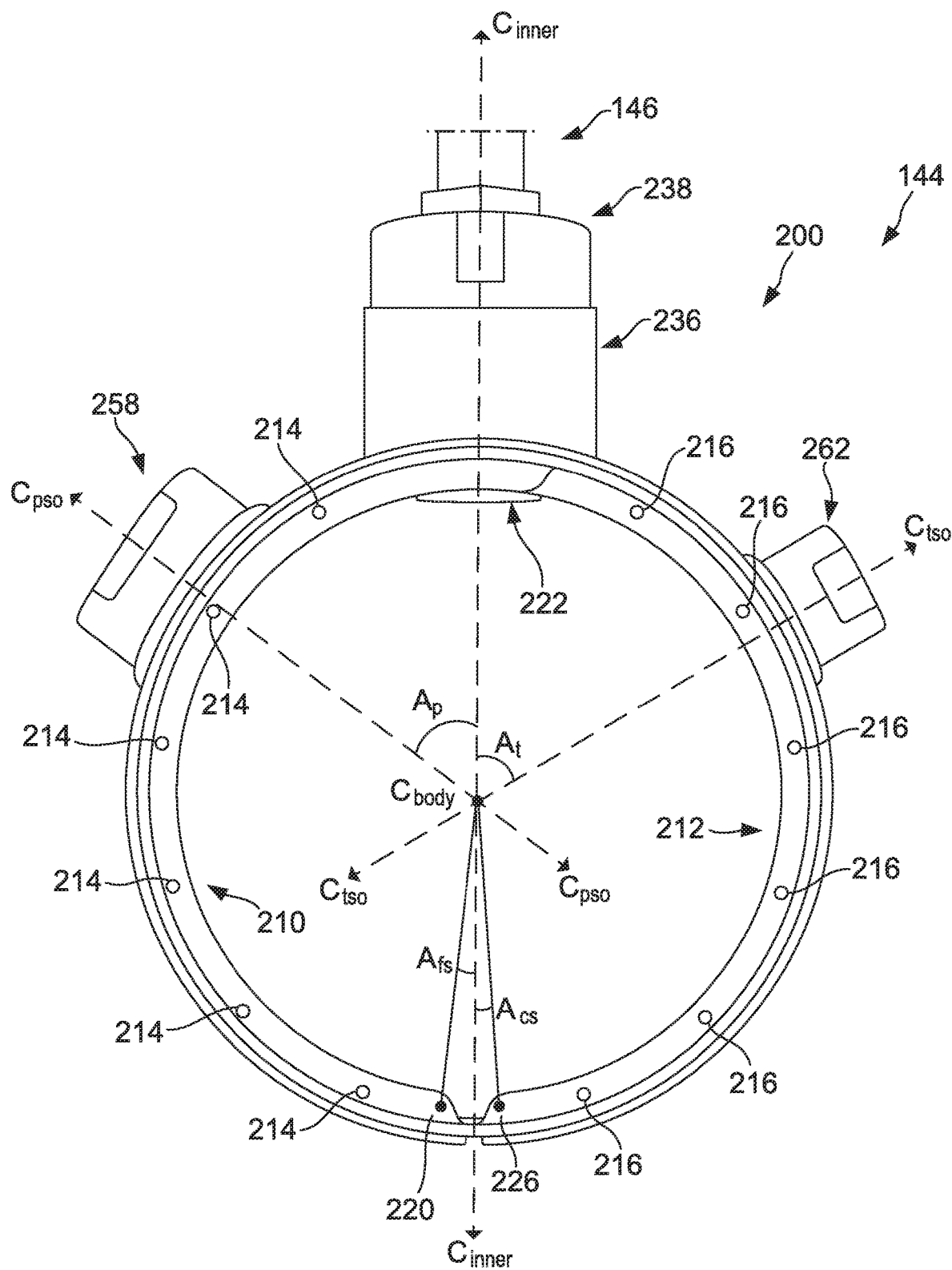
FIG. 4 is a front view of the example sampling assembly shown in FIG. 2.
Figure 5:
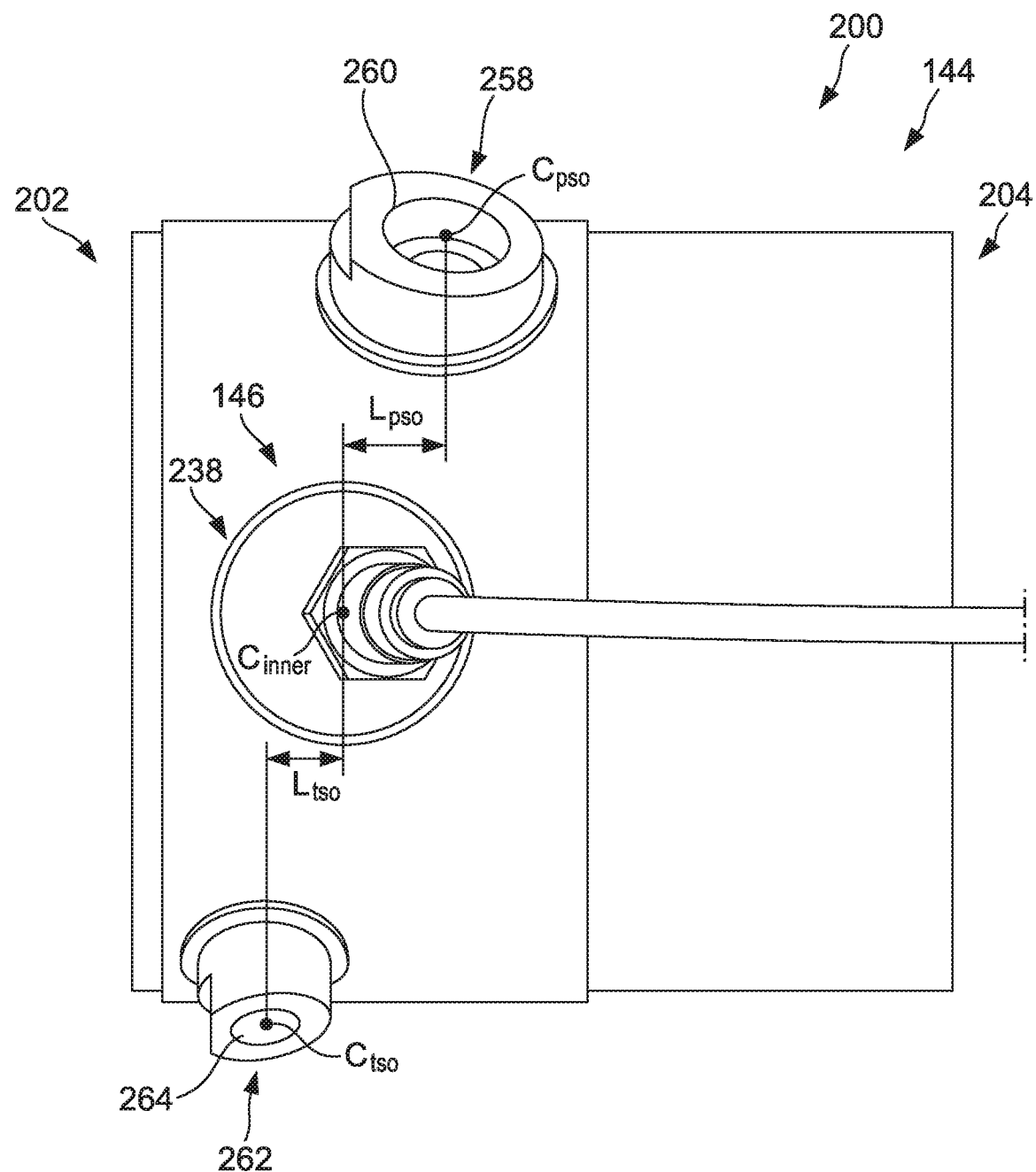
FIG. 5 is a top view of the example sampling assembly shown in FIG. 2.
Figure 6:
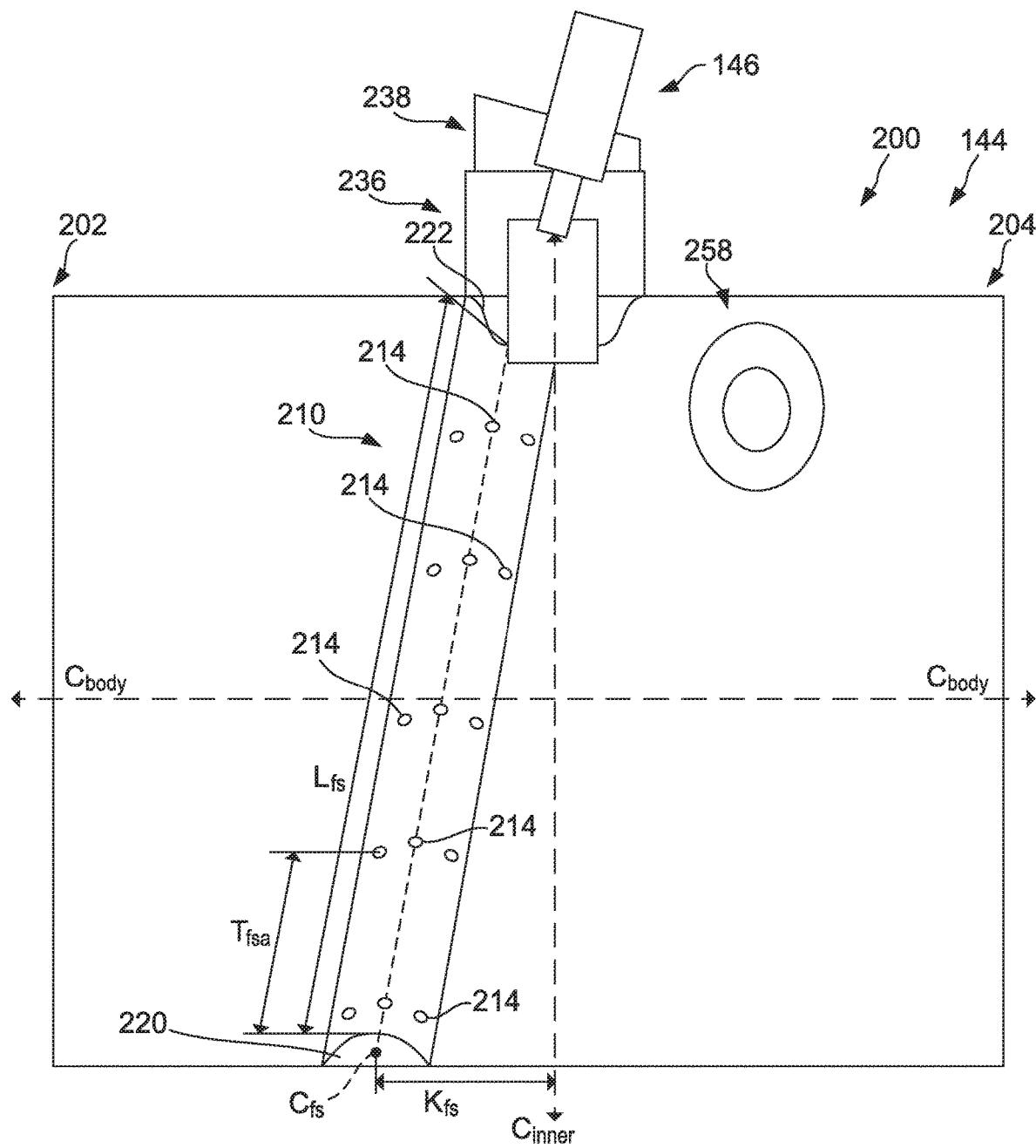
FIG. 6 is a cross-sectional view of the example sampling assembly shown in FIG. 2, taken along plane A-A.
Figure 7:
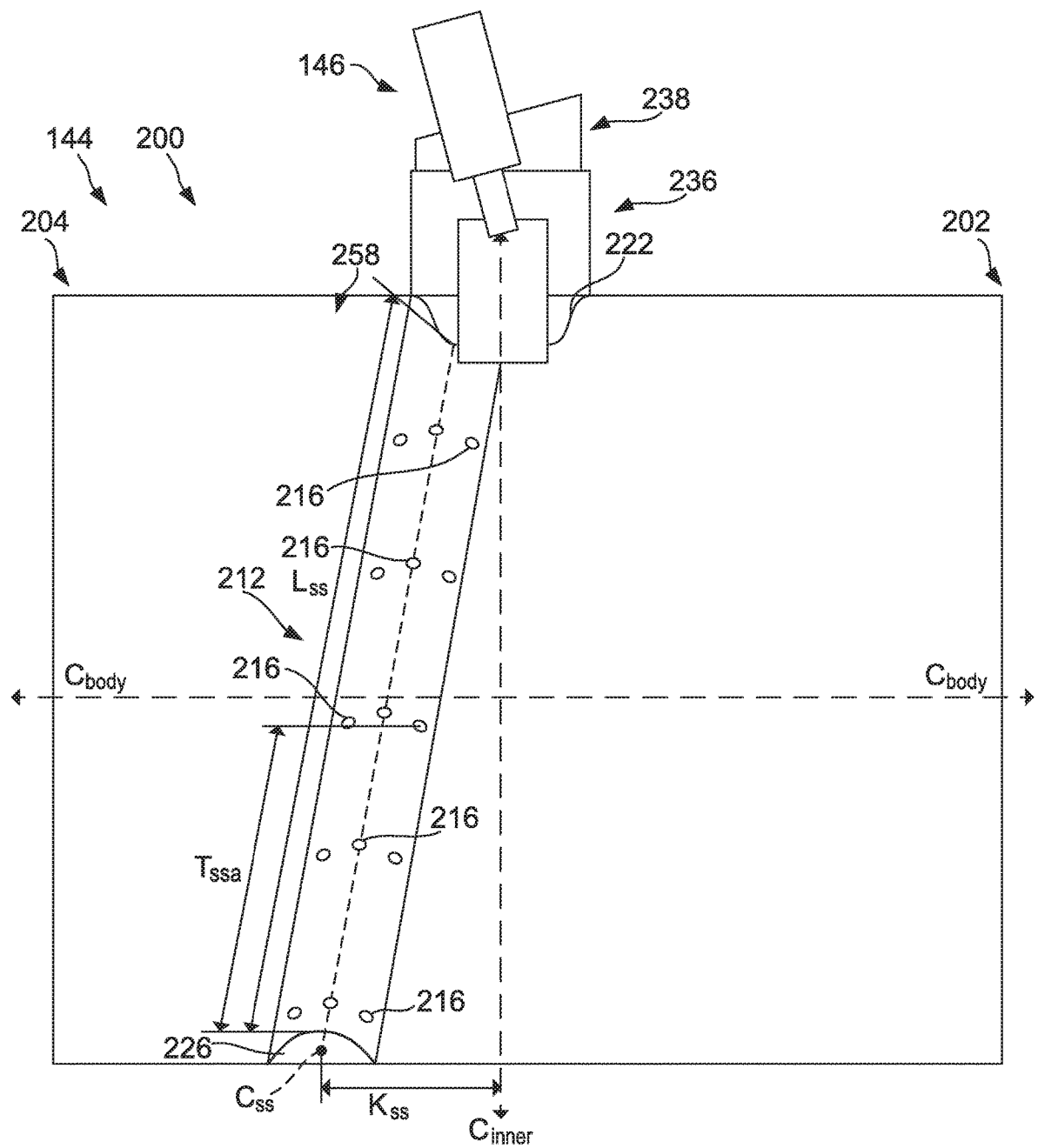
FIG. 7 is another cross-sectional view of the example sampling assembly shown in FIG. 2, taken along plane B-B.
Figure 8:
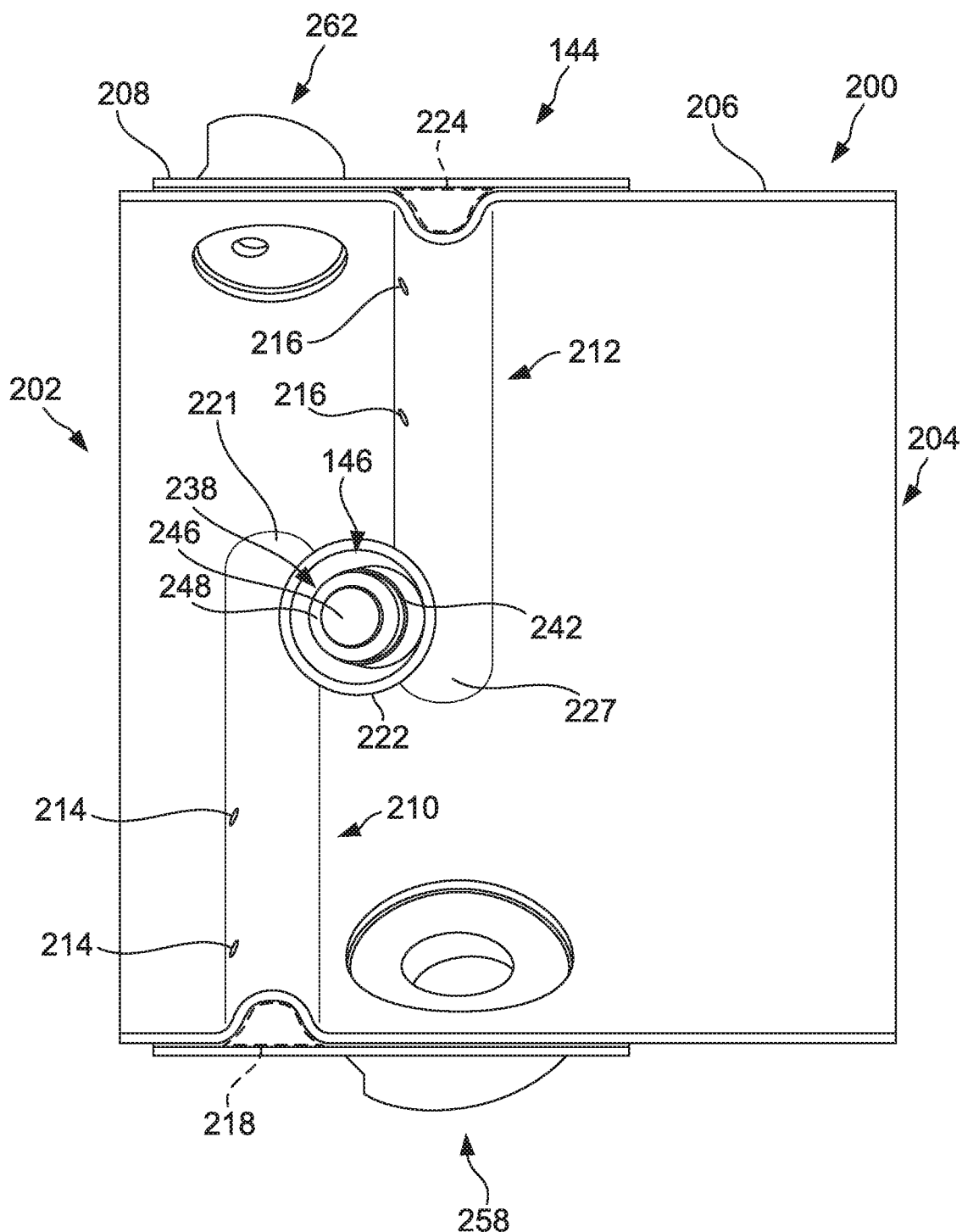
FIG. 8 is a cross-sectional view of the example sampling assembly shown in FIG. 2, taken along plane C-C.

As shown in FIGS. 9 and 10, the $H_s$ is greater than the $H_s$ of the sampling assembly body 200 shown in FIG. 3. As a result, the exhaust gas may flow from the outer bowl 236 into the inner bowl 232 without first flowing between the outer sensor shield 242 and the inner bowl 232. Such an arrangement may be advantageous in decreasing backpressure (e.g., an increase in pressure experienced by components of the exhaust gas aftertreatment system 100 that are upstream of the sampling assembly 144 due to the sampling assembly 144, etc.) in some applications.

The inner bowl 232 also includes an inner bowl flange 700 (e.g., lip, etc.). The inner bowl flange 700 is formed in a portion of the inner bowl 232 which is located outside of the outer bowl 236. As a result, the inner bowl flange 700 protrudes into the passage defined by the sampling assembly body 200. In various embodiments, the inner bowl flange 700 is formed by bending a portion of the inner bowl flange 700 radially outwards.

As exhaust gas flows through the passage defined by the sampling assembly body 200, a portion of the exhaust gas does not flow into the first sampler 210 or the second sampler 212. This portion of exhaust gas may contain liquid. The inner bowl flange 700 functions to mitigate the flow of this portion of exhaust gas into the inner bowl 232 by deflecting the flow of the exhaust gas.

FIG. 10 illustrates an embodiment where the inner bowl 232 includes a swirl vane 1000 coupled to an inner bowl inner surface 1002 of the inner bowl. The swirl vane 1000 helically extends (e.g., forms a helix, etc.) within the inner bowl 232 and defines a helical passage within which the exhaust gas from the outer bowl 236 may traverse to exit into the passage defined by the sampling assembly body 200. The swirl vane 1000 may function to enhance a swirl of the exhaust gas within the inner bowl 232, thereby further mitigating the transmission of liquid into the outer sensor shield 242. The swirl vane 1000 may additionally function to mitigate flow of the exhaust gas from the passage defined by the sampling assembly body 200 into the inner bowl 232 (e.g., thereby reducing impingement on the outer sensor shield 242, thereby reducing impingement on the sensor element 252, etc.).

V. Third Example Sampling Assembly

Figure 11:
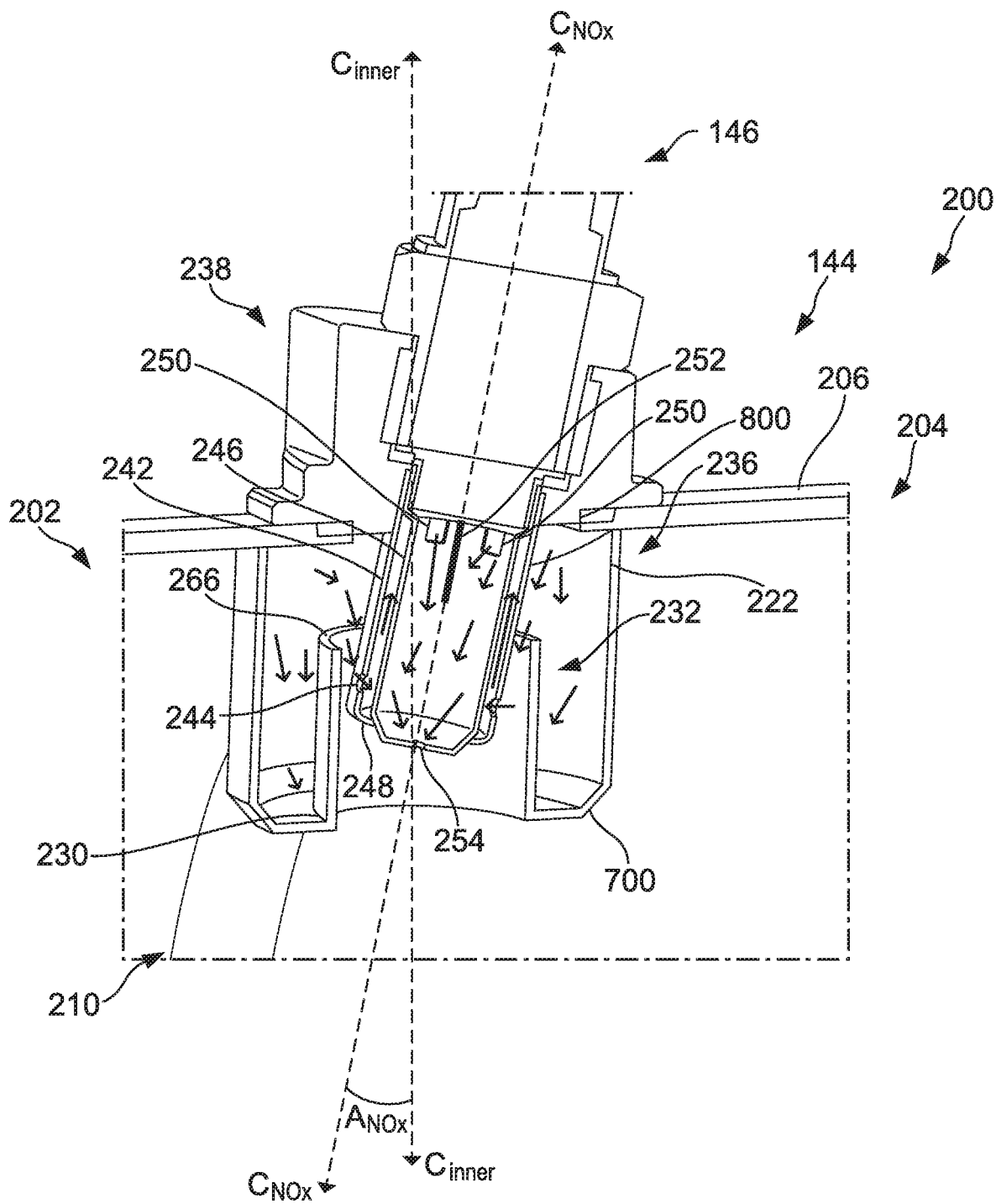
FIG. 11 is a detailed cross-sectional view of yet another example sampling assembly for an exhaust gas aftertreatment system.
Figure 12:
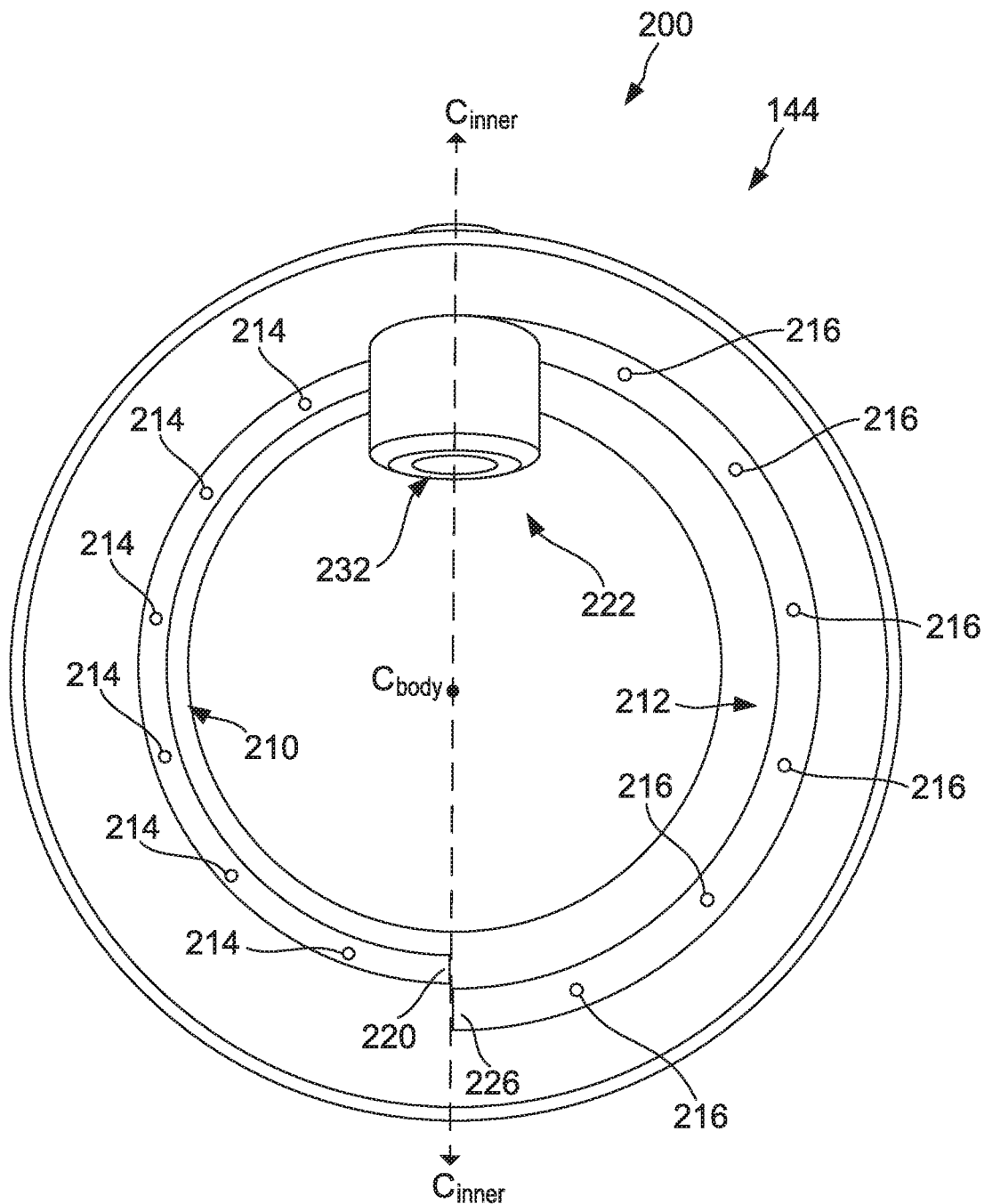
FIG. 12 is a front view of the example sampling assembly shown in FIG. 11.

FIGS. 11 and 12 illustrate an example sampling assembly 144 with the sampling assembly body 200 according to various embodiments. The foregoing description of the sampling assembly 144 with respect to FIGS. 2-8 similarly applies to the sampling assembly 144 illustrated in FIGS. 11 and 12.

The sampling assembly body 200 is configured such that the sampler channel collector 222 is a portion of the outer bowl 236 (e.g., the sampler channel collector 222 is structurally integrated with the outer bowl 236, etc.). Unlike in FIGS. 9 and 10, the entirety of the outer bowl 236 is located within the base body layer 206.

As a result of the placement of the outer bowl 236 within the base body layer 206, the exhaust gas flows from the first sampler channel 218 and the second sampler channel 224 into the outer bowl 236 at a location that is radially outward (e.g., relative to $C_{body}$, etc.) of the inner bowl top edge 266. This may cause the exhaust gas flowing into the outer bowl 236 to be provided into the inner bowl 232 more rapidly than in other embodiments, such as that illustrated in FIG. 3, where the exhaust gas flows from the first sampler channel 218 and the second sampler channel 224 into the outer bowl 236 at a location that is radially inward (e.g., relative to $C_{body}$, etc.) of the inner bowl top edge 266. This arrangement of the outer bowl 236 and the sampler channel collector 222 may decrease backpressure and eliminate the need for the wrap body layer 208, thereby decreasing the cost of the sampling assembly body.

The base body layer 206 includes a $NO_x$ sensor coupler opening 800. The $NO_x$ sensor coupling 238 extends through the $NO_x$ sensor coupler opening 800 and is coupled to the base body layer 206 about the $NO_x$ sensor coupler opening 800. In some embodiments, the $NO_x$ sensor coupling 238 is welded to the base body layer 206. In other embodiments, the $NO_x$ sensor coupling 238 is threaded into the $NO_x$ sensor coupler opening 800. In still other embodiments, the $NO_x$ sensor coupling 238 is press fit into the $NO_x$ sensor coupler opening 800 (e.g., via a friction fit, etc.).

As shown in FIGS. 11 and 12, the $H_s$ is less than the $H_s$ of the sampling assembly body 200 shown in FIGS. 9 and 10. As a result, the exhaust gas cannot flow from the outer bowl 236 into the inner bowl 232 without first flowing between the outer sensor shield 242 and the inner bowl 232.

In some embodiments, the sampling assembly body 200 includes only the base body layer 206 and does not include the wrap body layer 208.

VI. Construction of Example Embodiments

While this specification contains many specific implementation details, these should not be construed as limitations on the scope of what may be claimed but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described as acting in certain combinations and even initially claimed as such, one or more features from a claimed combination can, in some cases, be excised from the combination, and the claimed combination may be directed to a subcombination or variation of a subcombination.

As utilized herein, the terms "substantially," "generally," "approximately," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The term "coupled" and the like, as used herein, mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another, with the two components, or with the two components and any additional intermediate components being attached to one another.

The terms "fluidly coupled to" and the like, as used herein, mean the two components or objects have a pathway formed between the two components or objects in which a fluid, such as air, exhaust gas, liquid reductant, gaseous reductant, aqueous reductant, gaseous ammonia, etc., may flow, either with or without intervening components or objects. Examples of fluid couplings or configurations for enabling fluid communication may include piping, channels, or any other suitable components for enabling the flow of a fluid from one component or object to another.

It is important to note that the construction and arrangement of the system shown in the various example implementations is illustrative only and not restrictive in character. All changes and modifications that come within the spirit and/or scope of the described implementations are desired to be protected. It should be understood that some features may not be necessary, and implementations lacking the various features may be contemplated as within the scope of the application, the scope being defined by the claims that follow. When the language "a portion" is used, the item can include a portion and/or the entire item unless specifically stated to the contrary.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

Additionally, the use of ranges of values (e.g., W to P, etc.) herein are inclusive of their maximum values and minimum values (e.g., W to P includes W and includes P, etc.), unless otherwise indicated. Furthermore, a range of values (e.g., W to P, etc.) does not necessarily require the inclusion of intermediate values within the range of values (e.g., W to P can include only W and P, etc.), unless otherwise indicated.

What is claimed is:

1. A sampling assembly for an exhaust gas aftertreatment system, the sampling assembly comprising:
a body layer defining a cylindrical passage;
an outer bowl coupled to the body layer;
a first sampler extending circumferentially along the body layer to the outer bowl and disposed within the cylindrical passage, the first sampler comprising:
a first sampler channel extending circumferentially and configured to provide exhaust gas into the outer bowl, and
a first sampler aperture configured to receive the exhaust gas from the cylindrical passage and provide the exhaust gas into the first sampler channel; and
an inner bowl disposed at least partially within the outer bowl and configured to receive the exhaust gas from the outer bowl and provide the exhaust gas into the cylindrical passage.

2. The sampling assembly of claim 1, wherein:
the body layer is defined by a sampling assembly body center axis;
the inner bowl is defined by an inner bowl center axis; and
the inner bowl center axis intersects the sampling assembly body center axis.

3. The sampling assembly of claim 2, wherein the inner bowl center axis is orthogonal to the sampling assembly body center axis.

4. The sampling assembly of claim 2, wherein the outer bowl is centered on the inner bowl center axis.

5. The sampling assembly of claim 1, further comprising:
a NOx sensor; and
a NOx sensor coupling coupled to the outer bowl and comprising a NOx sensor coupling opening configured to receive the NOx sensor such that a portion of the NOx sensor is positioned within the outer bowl.

6. The sampling assembly of claim 5, wherein:
the NOx sensor coupling opening is defined by a NOx sensor coupling opening center axis;
the NOx sensor coupling is configured to be coupled to the outer bowl in a plurality of rotational positions; and
the NOx sensor coupling opening center axis does not intersect the inner bowl in any of the plurality of rotational positions.

7. The sampling assembly of claim 6, wherein the plurality of rotational positions comprises:
a first rotational position;
a second rotational position separated from the first rotational position by at least 90 degrees; and
a third rotational position separated from the first rotational position by at least 180 degrees.

8. The sampling assembly of claim 1, further comprising a sampler channel collector configured to receive the exhaust gas from the first sampler and to provide the exhaust gas into the outer bowl, the sampler channel collector coupled to the first sampler along an axis that is parallel to a tangent of the sampler channel collector such that the exhaust gas provided from the first sampler is provided into the sampler channel collector tangentially.

9. The sampling assembly of claim 1, further comprising a second sampler extending circumferentially along the body layer to the outer bowl, the second sampler comprising:

a second sampler channel extending circumferentially and configured to provide exhaust gas into the outer bowl, and
a second sampler aperture configured to receive the exhaust gas from the cylindrical passage and provide the exhaust gas into the second sampler channel.

10. The sampling assembly of claim 9, wherein the first sampler and the second sampler are identical.

11. The sampling assembly of claim 9, wherein:
the first sampler extends a first length between a first sampler first end and the outer bowl;
the second sampler extends a second length between a second sampler first end and the outer bowl; and
the second length is substantially equal to the first length.

12. The sampling assembly of claim 11, wherein:
the body layer is defined by a sampling assembly body center axis;
the inner bowl is defined by an inner bowl center axis;
the inner bowl center axis intersects the sampling assembly body center axis;
the first sampler first end is disposed upstream of the inner bowl center axis; and
the second sampler first end is disposed downstream of the inner bowl center axis.

13. The sampling assembly of claim 5, wherein the NOx sensor coupling is configured to be coupled to the outer bowl in a plurality of rotational positions comprising:
a first rotational position;
a second rotational position separated from the first rotational position by at least 90 degrees; and
a third rotational position separated from the first rotational position by at least 180 degrees.

14. A sampling assembly for use with a NOx sensor, the sampling assembly comprising:
a first body layer defining a cylindrical passage;
an outer bowl coupled to the first body layer and configured to receive exhaust gas and provide the exhaust gas to the cylindrical passage;
a first sampler disposed within the cylindrical passage and extending circumferentially along the first body layer to the outer bowl, the first sampler comprising:
a first sampler channel extending circumferentially and configured to provide the exhaust gas into the outer bowl, and
a first sampler aperture configured to receive the exhaust gas from the cylindrical passage and provide the exhaust gas into the first sampler channel; and
a NOx sensor coupling coupled to the outer bowl and comprising a NOx sensor coupling opening configured to receive the NOx sensor.

15. The sampling assembly of claim 14, further comprising a second body layer overlapping at least a portion of the first body layer;
wherein the first sampler is formed from the first body layer; and
wherein the first sampler channel is defined between the first body layer and the second body layer.

16. The sampling assembly of claim 14, further comprising a sampler channel collector configured to receive the exhaust gas from the first sampler and to provide the exhaust gas into the outer bowl, the sampler channel collector coupled to the first sampler along an axis that is parallel to a tangent of the sampler channel collector such that the exhaust gas provided from the first sampler is provided into the sampler channel collector tangentially.

17. The sampling assembly of claim 16, wherein at least one of the outer bowl and the sampler channel collector protrude into the cylindrical passage.

18. A sampling assembly comprising:
a body layer defining a cylindrical passage;
an outer bowl coupled to the body layer and configured to receive exhaust gas and provide the exhaust gas to the cylindrical passage;
a first sampler extending circumferentially along the body layer to the outer bowl, the first sampler comprising:
   a first sampler channel extending circumferentially and configured to provide the exhaust gas into the outer bowl, and
   a plurality of first sampler apertures, each of the plurality of first sampler apertures configured to receive the exhaust gas from the cylindrical passage and provide the exhaust gas into the first sampler channel; and
a second sampler extending circumferentially along the body layer to the outer bowl, the second sampler comprising:
   a second sampler channel extending circumferentially and configured to provide exhaust gas into the outer bowl, and
   a plurality of second sampler apertures, each of the plurality of second sampler apertures configured to receive the exhaust gas from the cylindrical passage and provide the exhaust gas into the second sampler channel;
wherein at least one of the first sampler or the second sampler is disposed within the cylindrical passage.

19. The sampling assembly of claim 18, further comprising a sampler channel collector configured to receive the exhaust gas from the first sampler and the second sampler and to provide the exhaust gas into the outer bowl, the sampler channel collector being coupled to the first sampler along a first axis that is parallel to a first tangent of the sampler channel collector such that the exhaust gas provided from the first sampler is provided into the sampler channel collector tangentially and coupled to the second sampler along a second axis that is parallel to a second tangent of the sampler channel collector such that the exhaust gas provided from the second sampler is provided into the sampler channel collector tangentially.

20. The sampling assembly of claim 19, further comprising an inner bowl disposed at least partially within the outer bowl and configured to receive the exhaust gas from the outer bowl and provide the exhaust gas into the cylindrical passage;
wherein the first axis extends between the inner bowl and the sampler channel collector; and
wherein the second axis extends between the inner bowl and the sampler channel collector.

* * * * *